US008097428B2

(12) United States Patent
Grompe et al.

(10) Patent No.: US 8,097,428 B2
(45) Date of Patent: Jan. 17, 2012

(54) MONOCLONAL ANTIBODIES AND THEIR USE

(75) Inventors: Markus Grompe, Portland, OR (US); Philip R. Streeter, Portland, OR (US); Craig Dorrell, Portland, OR (US); Stephanie L. Abraham, Clancy, MT (US); Kelsea M. Shoop, Oregon City, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 13/010,737

(22) Filed: Jan. 20, 2011

(65) Prior Publication Data

US 2011/0165080 A1 Jul. 7, 2011

Related U.S. Application Data

(62) Division of application No. 12/298,761, filed as application No. PCT/US2007/010466 on Apr. 27, 2007, now Pat. No. 7,981,628.

(60) Provisional application No. 60/795,900, filed on Apr. 28, 2006.

(51) Int. Cl.
*G01N 33/567* (2006.01)

(52) U.S. Cl. ............ 435/7.21; 435/320.1; 435/325; 435/326; 435/332; 536/23.5; 424/152.1; 530/387.1; 530/387.3; 530/388.2; 530/391.3; 530/391.7

(58) Field of Classification Search ........... 530/387.1, 530/387.3, 388.2, 391.3, 391.7; 536/23.5; 424/152.1; 435/7.21, 320.1, 325, 326, 332
See application file for complete search history.

(56) References Cited

FOREIGN PATENT DOCUMENTS

| EP | 1 090 927 | 4/2001 |
|---|---|---|
| WO | WO 03/000021 | 1/2003 |
| WO | WO 2005/033126 | 4/2005 |

OTHER PUBLICATIONS

Dorrell et al., "Isolation of major pancreatic cell types and long-term culture-initiating cells using novel human surface markers," *Stem Cell Res.* 1(3):183-194 (Sep. 2008).
Gaisano et al., "SNAP-23 is located in the basolateral plasma membrane of a rat pancreatic acinar cells," *FEBS Letters*, 414(2):298-302 (Sep. 8, 1997).
Gmyr et al., "Rapid purification of human ductal cells from human pancreatic fractions with surface antibody CA19-9," *Biochemical and Biophysical Research Communications*, 300(1):27-33 (Jul. 16, 2004).
Kobayashi et al., "Expression of glucose transporter 4 in the human pancreatic islet of Langerhans," *Biochemical and Biophysical Research Communications*, 314(4):1121-1125 (Feb. 20, 2004).
Palumbo et al., "Human aspartyl (asparaginyl) beta-hydroxylase monoclonal pancreatic carcinoma," *Pancreas*, 25(1):39-44 (Jul. 1, 2002).

*Primary Examiner* — Stephen Rawlings
(74) *Attorney, Agent, or Firm* — Klarquist Sparkman, LLP

(57) ABSTRACT

Isolated monoclonal antibodies are disclosed herein that specifically bind a cell surface antigen expressed on the human pancreatic endocrine cells or a subset thereof, and/or a precursor thereof. Isolated monoclonal antibodies are also disclosed herein that specifically bind a cell surface antigen expressed on human pancreatic exocrine cells or human ductal cells. Humanized forms of these antibodies, and functional fragments of these antibodies, are also disclosed. The antibodies can be conjugated to an effector molecule, such as a detectable marker, a therapeutic agent, or a toxin. These antibodies are of use to detect and isolate pancreatic cells or a subset thereof. The antibodies can be used for in vitro or in vivo detection and/or isolation of pancreatic endocrine cells. Methods of treating a pancreatic tumor are also disclosed. In several examples, the isolated monoclonal antibodies bind pancreatic endocrine cells and can be used to detect diabetes or a pancreatic endocrine cell tumor.

32 Claims, 5 Drawing Sheets

SEQUENCE LISTING

<160> NUMBER OF SEQ ID NOS: 40

<210> SEQ ID NO 1
<211> LENGTH: 5
<212> TYPE: PRT
<213> ORGANISM: Mus musculus

<400> SEQUENCE: 1

Asp Tyr Tyr Ile His
1               5

<210> SEQ ID NO 2
<211> LENGTH: 17
<212> TYPE: PRT
<213> ORGANISM: Mus musculus

<400> SEQUENCE: 2

Trp Ile Asp Pro Glu Asn Gly Asn Thr Ile Tyr Asp Pro Lys Phe Gln
1               5                   10                  15

Asp

<210> SEQ ID NO 3
<211> LENGTH: 10
<212> TYPE: PRT
<213> ORGANISM: Mus musculus

<400> SEQUENCE: 3

Tyr Tyr Gly Ser Thr Tyr Tyr Phe Asp Tyr
1               5                   10

<210> SEQ ID NO 4
<211> LENGTH: 5
<212> TYPE: PRT
<213> ORGANISM: Mus musculus

<400> SEQUENCE: 4

Glu Tyr Ile Ile His
1               5

<210> SEQ ID NO 5
<211> LENGTH: 17
<212> TYPE: PRT
<213> ORGANISM: Mus musculus

<400> SEQUENCE: 5

Trp Phe Tyr Pro Gly Ser Gly Gly Leu Lys Tyr Ser Glu Lys Phe Lys
1               5                   10                  15

Asp

<210> SEQ ID NO 6
<211> LENGTH: 7
<212> TYPE: PRT
<213> ORGANISM: Mus musculus

<400> SEQUENCE: 6

His Glu Lys Tyr Phe Asp Tyr
1               5

<210> SEQ ID NO 7
<211> LENGTH: 5
<212> TYPE: PRT
<213> ORGANISM: Mus musculus

<400> SEQUENCE: 7

Asn Tyr Ala Met Ser
1               5

<210> SEQ ID NO 8
<211> LENGTH: 17
<212> TYPE: PRT

<213> ORGANISM: Mus musculus

<400> SEQUENCE: 8

Thr Ile Ser Ser Gly Gly Ser Tyr Thr Tyr Tyr Pro Asp Ser Val Lys
1               5                   10                  15

Gly

<210> SEQ ID NO 9
<211> LENGTH: 10
<212> TYPE: PRT
<213> ORGANISM: Mus musculus

<400> SEQUENCE: 9

Gln Gly Asp Asn Tyr Trp Tyr Phe Asp Val
1               5                   10

<210> SEQ ID NO 10
<211> LENGTH: 5
<212> TYPE: PRT
<213> ORGANISM: Mus musculus

<400> SEQUENCE: 10

Asp Tyr Tyr Met His
1               5

<210> SEQ ID NO 11
<211> LENGTH: 18
<212> TYPE: PRT
<213> ORGANISM: Mus musculus

<400> SEQUENCE: 11

Phe Ile Arg Asn Lys Ala Asn Gly Tyr Thr Thr Glu Tyr Ser Ala Ser
1               5                   10                  15

Val Gly

<210> SEQ ID NO 12
<211> LENGTH: 6
<212> TYPE: PRT
<213> ORGANISM: Mus musculus

<400> SEQUENCE: 12

Asp Ile Lys Gly Asp Tyr
1               5

<210> SEQ ID NO 13
<211> LENGTH: 5
<212> TYPE: PRT
<213> ORGANISM: Mus musculus

<400> SEQUENCE: 13

Ser Tyr Asp Met Ser
1               5

<210> SEQ ID NO 14
<211> LENGTH: 17
<212> TYPE: PRT
<213> ORGANISM: Mus musculus

<400> SEQUENCE: 14

Tyr Ile Ser Ser Gly Gly Gly Ser Thr Tyr Phe Pro Asn Thr Val Lys
1               5                   10                  15

Gly

<210> SEQ ID NO 15
<211> LENGTH: 10
<212> TYPE: PRT
<213> ORGANISM: Mus musculus

<400> SEQUENCE: 15

His Gly Gly Asn Gln Pro Trp Phe Ala Tyr
1               5                   10

<210> SEQ ID NO 16
<211> LENGTH: 122
<212> TYPE: PRT
<213> ORGANISM: Mus musculus

<400> SEQUENCE: 16

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Asn Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Gly Asp Asn Tyr Trp Tyr Phe Asp Val Trp Gly Ala Gly
            100                 105                 110

Thr Thr Val Thr Val Ser Ser Glu Ser Gln
        115                 120

<210> SEQ ID NO 17
<211> LENGTH: 110
<212> TYPE: PRT
<213> ORGANISM: Mus musculus

<400> SEQUENCE: 17

Val Gln Leu Gln Gln Ser Gly Ala Glu Leu Val Lys Pro Gly Ala Ser
1               5                   10                  15

Val Lys Leu Ser Cys Lys Ala Ser Gly Tyr Thr Phe Thr Glu Tyr Ile
                20                  25                  30

Ile His Trp Val Lys Gln Arg Ser Gly Gln Gly Leu Glu Trp Ile Gly
            35                  40                  45

Trp Phe Tyr Pro Gly Ser Gly Leu Lys Tyr Ser Glu Lys Phe Lys
        50                  55                  60

Asp Lys Ala Thr Leu Thr Ala Asp Lys Ser Ser Ser Thr Val Tyr Met
65                  70                  75                  80

Glu Leu Ser Arg Leu Thr Ser Glu Asp Ser Ala Val Tyr Phe Cys Ala
                85                  90                  95

Arg His Glu Lys Tyr Phe Asp Tyr Trp Gly Gln Gly Thr Thr
            100                 105                 110

<210> SEQ ID NO 18
<211> LENGTH: 112
<212> TYPE: PRT
<213> ORGANISM: Mus musculus

<400> SEQUENCE: 18

Glu Val Lys Leu Val Glu Ser Gly Gly Gly Leu Val Gln Pro Gly Gly

```
                1               5                   10                  15
Ser Leu Arg Leu Ser Cys Ala Thr Ser Gly Phe Thr Phe Thr Asp Tyr
                20                  25                  30

Tyr Met His Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Ile Lys Gly Asp Tyr Trp Gly Gln Gly Thr Ser
            100                 105                 110

<210> SEQ ID NO 19
<211> LENGTH: 113
<212> TYPE: PRT
<213> ORGANISM: Mus musculus

<400> SEQUENCE: 19

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Ala Phe Ser Ser Tyr
                20                  25                  30

Asp Met Ser Trp Val Arg Gln Ala Pro Asp Lys Arg Leu Glu Trp Val
            35                  40                  45

Ala Tyr Ile Ser Ser Gly Gly Gly Ser Thr Tyr Phe Pro Asn Thr Val
        50                  55                  60

Lys Gly Arg Phe Thr Ile Ser Arg Asp Asn Ala Lys Asn Thr Leu Ser
65                  70                  75                  80

Leu Gln Met Ser Ser Leu Arg Ser Glu Asp Thr Ala Met Tyr Tyr Cys
                85                  90                  95

Thr Arg His Gly Gly Asn Gln Pro Trp Phe Ala Tyr Trp Gly Gln Gly
            100                 105                 110

Thr

<210> SEQ ID NO 20
<211> LENGTH: 23
<212> TYPE: PRT
<213> ORGANISM: Homo sapiens

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 21
<211> LENGTH: 14
<212> TYPE: PRT
<213> ORGANISM: Homo sapiens

<400> SEQUENCE: 21

Trp Tyr Gln Gln Lys Pro Gly Gln Pro Pro Leu Leu Ile Tyr
1               5                   10

<210> SEQ ID NO 22
<211> LENGTH: 32
<212> TYPE: PRT
```

<213> ORGANISM: Homo sapiens

<400> SEQUENCE: 22

```
Gly Val Pro Asp Arg Pro Phe Gly Ser Gly Ser Gly Thr Asp Phe Thr
1               5                   10                  15
Leu Thr Ile Ser Ser Leu Gln Ala Glu Asp Val Ala Val Tyr Tyr Cys
            20                  25                  30
```

<210> SEQ ID NO 23
<211> LENGTH: 11
<212> TYPE: PRT
<213> ORGANISM: Homo sapiens

<400> SEQUENCE: 23

```
Phe Gly Gln Gly Gln Thr Lys Leu Glu Ile Lys
1               5                   10
```

<210> SEQ ID NO 24
<211> LENGTH: 30
<212> TYPE: PRT
<213> ORGANISM: Homo sapiens

<400> SEQUENCE: 24

```
Gln Val Gln Leu Val Gln Ser Gly Ala Glu Val Lys Lys Pro Gln Ala
1               5                   10                  15
Ser Val Lys Val Ser Cys Lys Ala Ser Gln Tyr Thr Phe Thr
            20                  25                  30
```

<210> SEQ ID NO 25
<211> LENGTH: 14
<212> TYPE: PRT
<213> ORGANISM: Homo sapiens

<400> SEQUENCE: 25

```
Trp Val Arg Gln Ala Pro Gly Gln Arg Leu Glu Trp Met Gly
1               5                   10
```

<210> SEQ ID NO 26
<211> LENGTH: 32
<212> TYPE: PRT
<213> ORGANISM: Homo sapiens

<400> SEQUENCE: 26

```
Arg Val Thr Ile Thr Arg Asp Thr Ser Ala Ser Thr Ala Tyr Met Glu
1               5                   10                  15
Leu Ser Ser Leu Arg Ser Glu Asp Thr Ala Val Tyr Tyr Cys Ala Arg
            20                  25                  30
```

<210> SEQ ID NO 27
<211> LENGTH: 11
<212> TYPE: PRT
<213> ORGANISM: Homo sapiens

<400> SEQUENCE: 27

```
Trp Gly Gln Gly Thr Leu Val Thr Val Ser Ser
1               5                   10
```

<210> SEQ ID NO 28
<211> LENGTH: 613
<212> TYPE: PRT
<213> ORGANISM: Pseudomonas aeruginosa

<400> SEQUENCE: 28

```
Ala Glu Glu Ala Phe Asp Leu Trp Asn Glu Cys Ala Lys Ala Cys Val
```

-continued

```
1               5               10              15
Leu Asp Leu Lys Asp Gly Val Arg Ser Ser Arg Met Ser Val Asp Pro
            20              25              30

Ala Ile Ala Asp Thr Asn Gly Gln Gly Val Leu His Tyr Ser Met Val
            35              40              45

Leu Glu Gly Gly Asn Asp Ala Leu Lys Leu Ala Ile Asp Asn Ala Leu
50              55              60

Ser Ile Thr Ser Asp Gly Leu Thr Ile Arg Leu Glu Gly Gly Val Glu
65              70              75              80

Pro Asn Lys Pro Val Arg Tyr Ser Tyr Thr Arg Gln Ala Arg Gly Ser
            85              90              95

Trp Ser Leu Asn Trp Leu Val Pro Ile Gly His Glu Lys Pro Ser Asn
            100             105             110

Ile Lys Val Phe Ile His Glu Leu Asn Ala Gly Asn Gln Leu Ser His
            115             120             125

Met Ser Pro Ile Tyr Thr Ile Glu Met Gly Asp Glu Leu Leu Ala Lys
            130             135             140

Leu Ala Arg Asp Ala Thr Phe Phe Val Arg Ala His Glu Ser Asn Glu
145             150             155             160

Met Gln Pro Thr Leu Ala Ile Ser His Ala Gly Val Ser Val Val Met
            165             170             175

Ala Gln Thr Gln Pro Arg Arg Glu Lys Arg Trp Ser Glu Trp Ala Ser
            180             185             190

Gly Lys Val Leu Cys Leu Leu Asp Pro Leu Asp Gly Val Tyr Asn Tyr
            195             200             205

Leu Ala Gln Gln Arg Cys Asn Leu Asp Asp Thr Trp Glu Gly Lys Ile
210             215             220

Tyr Arg Val Leu Ala Gly Asn Pro Ala Lys His Asp Leu Asp Ile Lys
225             230             235             240

Pro Thr Val Ile Ser His Arg Leu His Phe Pro Glu Gly Gly Ser Leu
            245             250             255

Ala Ala Leu Thr Ala His Gln Ala Cys His Leu Pro Leu Glu Thr Phe
            260             265             270

Thr Arg His Arg Gln Pro Arg Gly Trp Glu Gln Leu Glu Gln Cys Gly
            275             280             285

Tyr Pro Val Gln Arg Leu Val Ala Leu Tyr Leu Ala Ala Arg Leu Ser
            290             295             300

Trp Asn Gln Val Asp Gln Val Ile Arg Asn Ala Leu Ala Ser Pro Gly
305             310             315             320

Ser Gly Gly Asp Leu Gly Glu Ala Ile Arg Glu Gln Pro Glu Gln Ala
            325             330             335

Arg Leu Ala Leu Thr Leu Ala Ala Glu Ser Glu Arg Phe Val Arg
            340             345             350

Gln Gly Thr Gly Asn Asp Glu Ala Gly Ala Ala Asn Ala Asp Val Val
            355             360             365

Ser Leu Thr Cys Pro Val Ala Ala Gly Glu Cys Ala Gly Pro Ala Asp
            370             375             380

Ser Gly Asp Ala Leu Leu Glu Arg Asn Tyr Pro Thr Gly Ala Glu Phe
385             390             395             400

Leu Gly Asp Gly Gly Asp Val Ser Phe Ser Thr Arg Gly Thr Gln Asn
            405             410             415

Trp Thr Val Glu Arg Leu Leu Gln Ala His Arg Gln Leu Glu Glu Arg
            420             425             430
```

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 29
<211> LENGTH: 342
<212> TYPE: DNA
<213> ORGANISM: Mus musculus

<400> SEQUENCE: 29
cagaagttca gctgcagcag tctggggctg agcttgtgag gccaggggcc ttagtcaagt    60
tgtcctgcaa agcttctggc ttcaatatta agactacta tatacactgg gtgaagcaga   120
agcctgaaca gggcctggag tggattggat ggattgatcc tgagaatggt aatactatat   180
atgacccgaa gttccaggac aaggccagta aacttcaga cacatcctcc aacacagcct   240
acctccagct cagcagcctg acatctgagg acactgccgt ctattactgt actagttact   300
acggtagtac ctactacttt gactactggg gccaaggcac ca                     342

<210> SEQ ID NO 30
<211> LENGTH: 405
<212> TYPE: DNA
<213> ORGANISM: Mus musculus

<400> SEQUENCE: 30
atggcggcgg cgcagagcat tcaggtgcag attcagctgg tgcagagcgg cccggaactg    60
aaaaaaccgg gcgaaaccgt gaaaattagc tgcaaagcga gcggctatac ctttaccgat   120
tatagcatgc attgggtgaa acaggcgccg ggcaaaggcc tgaaatggat gggctggatt   180
aacaccgaaa ccggcgaacc gacctatgcg gatgatttta aaggccgctt tgcgtttagc   240
ctggaaacca gcgcgagcac cgcgtatctg cagattaaca acctgaaaaa cgaagatacc   300
gcgacctatt tttgcagccg cggctatggc agcagcagct ggtttgcgta ttggggccag   360
ggcaccctgg tgaccgtgag cgcggaaagc cagagctttc gaac                    405

<210> SEQ ID NO 31

<210> SEQ ID NO 31
<211> LENGTH: 369
<212> TYPE: DNA
<213> ORGANISM: Mus musculus

<400> SEQUENCE: 31

```
tgaagtgatg ctggtggagt ctgggggagg cttagtgaag cctggagggt ccctgaaact      60
ctcctgtgca gcctctggat tcactttcag taactatgcc atgtcttggg ttcgccagac     120
tccggagaag aggctggagt gggtcgcaac cattagtagt ggtggtagtt acacctacta     180
tccagacagt gtgaaggggc gattcaccat ctccagagac aatgccaaga cacccctgta     240
cctgcaaatg agcagtctga ggtctgagga cacggccatg tattactgtg caagacaggg     300
ggataactac tggtacttcg atgtctgggg cgcagggacc acggtcaccg tctcctcaga     360
gagtcagtc                                                             369
```

<210> SEQ ID NO 32
<211> LENGTH: 331
<212> TYPE: DNA
<213> ORGANISM: Mus musculus

<400> SEQUENCE: 32

```
gagtggtgcc ttggccccaa taatcaaaat acttctcgtg tcttgcacag aaatagaccg      60
cagagtcttc agatgtcaat ctactaagtt ccatatagac tgtgctggag gatttgtccg     120
cagtcaatgt ggccttgtcc ttgaatttct cactgtactt tagaccacca cttccagggt     180
aaaaccaccc aatccactca agaccctgtc cagacctctg cttacccag tgtataatat      240
actcagtgaa ggtgtagcca gaagccttgc aggacagctt cactgatgcc ccgggtttca     300
ccagctcagc tccagactgc tgcagctgga c                                     331
```

<210> SEQ ID NO 33
<211> LENGTH: 339
<212> TYPE: DNA
<213> ORGANISM: Mus musculus

<400> SEQUENCE: 33

```
tgaggtgaag ctggtggagt ctggaggagg cttggtacag cctgggggtt ctctgagact      60
ctcctgtgca acttctggat tcaccttcac tgattactac atgcactggg tccgccagcc     120
tccaggaaag gcacttgagt ggttgggttt tattagaaac aaagctaatg gttacacaac     180
agagtacagt gcatctgtga agggtcggtt caccatctcc agagataatt cccaaagcat     240
cctctatctt caaatgaaca ccctgagagc tgaggacagt gccacttatt actgtacaag     300
agatataaag ggggactact ggggtcaagg aacctcagt                             339
```

<210> SEQ ID NO 34
<211> LENGTH: 341
<212> TYPE: DNA
<213> ORGANISM: Mus musculus

<400> SEQUENCE: 34

```
gagtcccttg gccccaataa gcaaaccagg gttggttacc cccatgtctt gtacagtaat      60
acatggctgt gtcttcagac ctcagactgc tcatctgcag ggacagggtg ttcttggcat     120
tgtctctgga atggtgaat cggcccttca cagtgtttgg aaagtaggtg ctaccaccac      180
cactactaat gtatgcgacc cactccagcc tcttgtccgg agcctggcga acccaagaca     240
tgtcatagct actgaaagcg aatccagagg ctgcacagga gagtttcagg accctccag      300
gcttcactaa gcctccccca gactccacca gttgcacttc a                          341
```

```
<210> SEQ ID NO 35
<211> LENGTH: 6
<212> TYPE: PRT
<213> ORGANISM: Mus musculus

<400> SEQUENCE: 35

Thr Asp Tyr Ser Met His
1               5

<210> SEQ ID NO 36
<211> LENGTH: 15
<212> TYPE: PRT
<213> ORGANISM: Mus musculus

<400> SEQUENCE: 36

Asn Thr Glu Thr Gly Glu Pro Thr Tyr Ala Asp Asp Phe Lys Gly
1               5                   10                  15

<210> SEQ ID NO 37
<211> LENGTH: 10
<212> TYPE: PRT
<213> ORGANISM: Mus musculus

<400> SEQUENCE: 37

Gly Tyr Gly Ser Ser Ser Trp Phe Ala Tyr
1               5                   10

<210> SEQ ID NO 38
<211> LENGTH: 118
<212> TYPE: PRT
<213> ORGANISM: Mus musculus

<400> SEQUENCE: 38

Gln Val Gln Ile Gln Leu Val Gln Ser Gly Pro Glu Leu Lys Lys Pro
1               5                   10                  15

Gly Glu Thr Val Lys Ile Ser Cys Lys Ala Ser Gly Tyr Thr Phe Thr
                20                  25                  30

Asp Tyr Ser Met His Trp Val Lys Gln Ala Pro Gly Lys Gly Leu Lys
            35                  40                  45

Trp Met Gly Trp Ile Asn Thr Glu Thr Gly Glu Pro Thr Tyr Ala Asp
        50                  55                  60

Asp Phe Lys Gly Arg Phe Ala Phe Ser Leu Glu Thr Ser Ala Ser Thr
65                  70                  75                  80

Ala Tyr Leu Gln Ile Asn Asn Leu Lys Asn Glu Asp Thr Ala Thr Tyr
                85                  90                  95

Phe Cys Ser Arg Gly Tyr Gly Ser Ser Ser Trp Phe Ala Tyr Trp Gly
            100                 105                 110

Gln Gly Thr Leu Val Thr
        115

<210> SEQ ID NO 39
<211> LENGTH: 113
<212> TYPE: PRT
<213> ORGANISM: Mus musculus

<400> SEQUENCE: 39

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
                20                  25                  30

Tyr Ile His Trp Val Lys Gln Lys Pro Glu Gln Gly Leu Glu Trp Ile
```

```
                35                  40                  45
Gly Trp Ile Asp Pro Glu Asn Gly Asn Thr Ile Tyr Asp Pro Lys Phe
            50                  55                  60

Gln Asp Lys Ala Ser Ile Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Thr Ser Tyr Tyr Gly Ser Thr Tyr Tyr Phe Asp Tyr Trp Gly Gln Gly
            100                 105                 110

Thr

<210> SEQ ID NO 40
<211> LENGTH: 132
<212> TYPE: PRT
<213> ORGANISM: Mus musculus

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Glu Tyr
            20                  25                  30

Tyr Met His Trp Val Arg Gln Ala Pro Gly Lys Gly Leu Glu Trp Val
        35                  40                  45

Gly Leu Ile Asp Pro Glu Gln Gly Asn Thr Ile Tyr Asp Pro Lys Phe
    50                  55                  60

Gln Asp Arg Ala Thr Ile Ser Ala Asp Asn Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Thr Ala Ala Tyr Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser
    130
```

MONOCLONAL ANTIBODIES AND THEIR USE

CROSS REFERENCE TO RELATED APPLICATIONS

This application is a divisional of U.S. patent application Ser. No. 12/298,761, filed Oct. 27, 2008, now U.S. Pat. No. 7,981,628 which is the U.S. National Stage of PCT Application No. PCT/US2007/010466, filed Apr. 27, 2007, which was published in English under PCT Article 21(2), which in turn claims the benefit of U.S. Provisional Application No. 60/795,900, filed Apr. 28, 2006. The prior applications are incorporated herein by reference in their entirety.

STATEMENT OF GOVERNMENT SUPPORT

This invention was made with United States government support, pursuant to grant 1U01DK072477 from the National Institutes of Health (NIDDK). The United States government has certain rights in the invention.

FIELD

This application relates to the fields of diabetes and cancer, specifically to antibodies that specifically bind an antigen expressed on the surface of human pancreatic endocrine cells, exocrine cells, and ductal cells.

BACKGROUND

A mammalian pancreas is composed of two subclasses of tissue: the exocrine cells of the acinar tissue and the endocrine cells of the islets of Langerhans. The exocrine cells produce digestive enzymes that are secreted through the pancreatic duct to the intestine. The islet cells produce polypeptide hormones that are involved in carbohydrate metabolism. The islands of endocrine tissue that exist within the adult mammalian pancreas are termed the islets of Langerhans. Adult mammalian islets are composed of four major cell types, the α, β, δ, and PP cells. These cells are distinguished by their production of glucagon, insulin, somatostatin, and pancreatic polypeptide, respectively.

Diabetes mellitus results from the failure of cells to transport endogenous glucose across their membranes either because of an endogenous deficiency of insulin or an insulin receptor defect. Diabetes type 1, or insulin dependent diabetes mellitus (IDDM) is caused by the destruction of β cells, which results in insufficient levels of endogenous insulin. Diabetes type 2, or non-insulin dependent diabetes, is believed to be a defect in either the insulin receptor itself or in the number of insulin receptors present or in the balance between insulin and glucagon signals. Although diabetes runs in families, and a variety of heritable mutations have been implicated in the development of the disease, no single genetic marker has been identified that is responsible for this condition.

Current treatment of individuals with clinical manifestation of diabetes attempts to emulate the role of the pancreatic β cells in a non-diabetic individual. Individuals with normal β cell function exhibit precise regulation of insulin secretion in response to serum glucose levels. This regulation is due to a feedback mechanism that resides in the β cells that ordinarily prevents surges of blood sugar outside of the normal limits. Unless blood sugar is controlled properly, dangerous or even fatal levels can result. Hence, treatment of a diabetic individual involves monitoring of blood glucose levels and the use of injected bovine, porcine, or cloned human insulin as required. Despite such intervention, there is often a gradual decline in the health of diabetics.

Diabetes afflicts millions of people in the United States alone, and there is a clear need to provide cells capable of replacing pancreatic endocrine function. The ability to isolate distinct populations of live pancreatic endocrine cells represents a key step towards achieving this goal. This permits in vitro modeling of the Islet of Langerhans, for the study of normal and aberrant glucose metabolism and facilitate the isolation and/or evaluation of β cells. In addition, there is a need to produce new clinical treatments for diabetes, including the production of islet cells for transplantation (see U.S. Pat. No. 4,439,521; U.S. Pat. No. 5,510,263; U.S. Pat. No. 5,646,035; U.S. Pat. No. 5,961,972). Successful transplants of whole isolated islets, for example, have been made in animals and in humans. The success of the Edmonton protocol in the treatment of type 1 diabetes highlighted the promise of cellular replacement therapy for this disorder (Hirshberg et al., Rev Endocr Metab Disord. 4:381-389, 2003; Sharpiro et al., N Engl J. Med. 343:230-238, 2000). Unfortunately, insulin independence has not necessarily been shown to be durable in transplant recipients.

There is a need to identify and isolate islet cells or islet progenitor cells that can be used for β cell expansion or differentiation in vitro or for direct transplantation. Furthermore, there is a need for diagnostic methods that can accurately assess the number of pancreatic endocrine cells (or a subset thereof) in a subject, such as a subject with type 1 or type 2 diabetes.

SUMMARY

Isolated monoclonal antibodies are disclosed herein that specifically bind a cell surface antigen expressed on distinct subsets of human pancreatic cells. In one embodiment, an antibody is provided that specifically bind endocrine cells or a subset thereof, and/or a precursor thereof. The antibody does not bind a pancreatic endocrine hormone, such as insulin, glucagon, somatostatin or pancreatic polypeptide, or their receptors, and do not bind pancreatic exocrine tissue. In another embodiment, a monoclonal antibody is provided that specifically binds a cell surface antigen on pancreatic duct cells. These antibodies do not bind endocrine or exocrine cells. In a third embodiment, a monoclonal antibody is disclosed that specifically binds a cell surface antigen on exocrine cells. The antibody does not bind endocrine or duct cells.

Humanized forms of these antibodies, and functional fragments of these antibodies, are also disclosed. The antibodies can be conjugated to an effector molecule, such as a detectable marker, a therapeutic agent, or a toxin.

In one example, the isolated monoclonal antibodies bind insulin-producing cell (β cells). In another example, the isolated monoclonal antibodies bind glucagon-producing cells (α cells). In additional examples, the isolated monoclonal antibodies bind a cell surface antigen that is expressed on the cell surface of one or more of insulin producing cells, somatostatin-producing cells, pancreatic polypeptide producing cells and glucagon producing cells. In a further example, the isolated monoclonal antibodies bind all types of pancreatic endocrine cells. These antibodies are of use to detect and isolate all pancreatic endocrine cells, or subsets of pancreatic endocrine cells. In several examples, the isolated monoclonal antibodies can be used to detect diabetes or a pancreatic endocrine cell tumor. In an additional embodiment, the isolated monoclonal antibodies bind a cell surface antigen on pancreatic ductal cells, and can be used to detect pancreatic adenocarcinoma. In a further embodiment, the isolated monoclonal antibodies bind a cell surface antigen on pancreatic exocrine cells, and can be used to detect a pancreatic exocrine tumor. The antibodies can be used for in vitro or in vivo detection of pancreatic cells or a subset thereof.

Methods of treating a pancreatic endocrine tumor, a pancreatic exocrine tumor, or a pancreatic adenocarcinoma are also disclosed herein. The method includes administering a therapeutically effective amount of one or more of these antibodies to a subject with the pancreatic tumor.

In additional embodiments, antibodies that specifically bind duct and exocrine can be used to isolate of purified populations of these cells to initiate cell cultures that can be modified to express insulin. Furthermore, methods for isolating purified populations of endocrine cells are disclosed, wherein positive selection for endocrine cells is combined with negative selection for markers of duct and exocrine cells.

The foregoing and other features and advantages will become more apparent from the following detailed description of several embodiments, which proceeds with reference to the accompanying figures.

BRIEF DESCRIPTION OF THE FIGURES

FIG. 3A is a schematic diagram of an antibody showing the disulfide linked heavy (H) and light (L) chains, and the location of regions within the ~110 amino acid variable (V) domains that show a high degree of sequence variation. These regions determine the antigen specificity and are called "hypervariable regions" or "complementarity determining regions," (CDRs). FIG. 3B is a bar graph illustrating the variability of the three hypervariable regions CDR1-CDR3, with sequence variability plotted as a function of residue number along the polypeptide chain. The three large peaks correspond to the three hypervariable regions in (A). FIG. 3C is the amino acid sequence of the HIC0 4-F9 monoclonal antibody $V_H$ (SEQ ID NO: 39) aligned with the humanized D3h44 Fab (SEQ ID NO: 40, PDB accession # 1JPT; 1.85 Å resolution). The intervening sequence is the amino acids that are identical in HIC0 4-F9 and D3h44 (SEQ ID NOs: 39 and 40). FIG. 3D is a ribbon diagram of the D3h44 $Fv_H$. The structure is based on the crystallographic coordinates of the D3h44 Fab (PDB accession code 1JPT). The amino and carboxyl termini of the D3h44 $Fv_H$ are labeled N, C, respectively. The conserved cysteines that comprise the disulfide bond are rendered as space-filled models, and the hypervariable regions CDR1-CDR3 are indicated as loops 1, 2, and 3, with the framework regions also indicated FIG. 4A shows the non-specific cell fluorescence associated with random binding of the secondary antibody alone. FIGS. 4B-D show the binding of HIC1 7-H10 in the pre-sort population, negatively sorted population and positively sorted population respectively. Sorting and analysis of these cells was performed using a Cytopeia Influx™. Detection of the primary antibody labeling was achieved with an APC-conjugated $F(ab')_2$ fragment of goat anti-mouse immunoglobulin (H+L).

SEQUENCE LISTING

Figure 1:
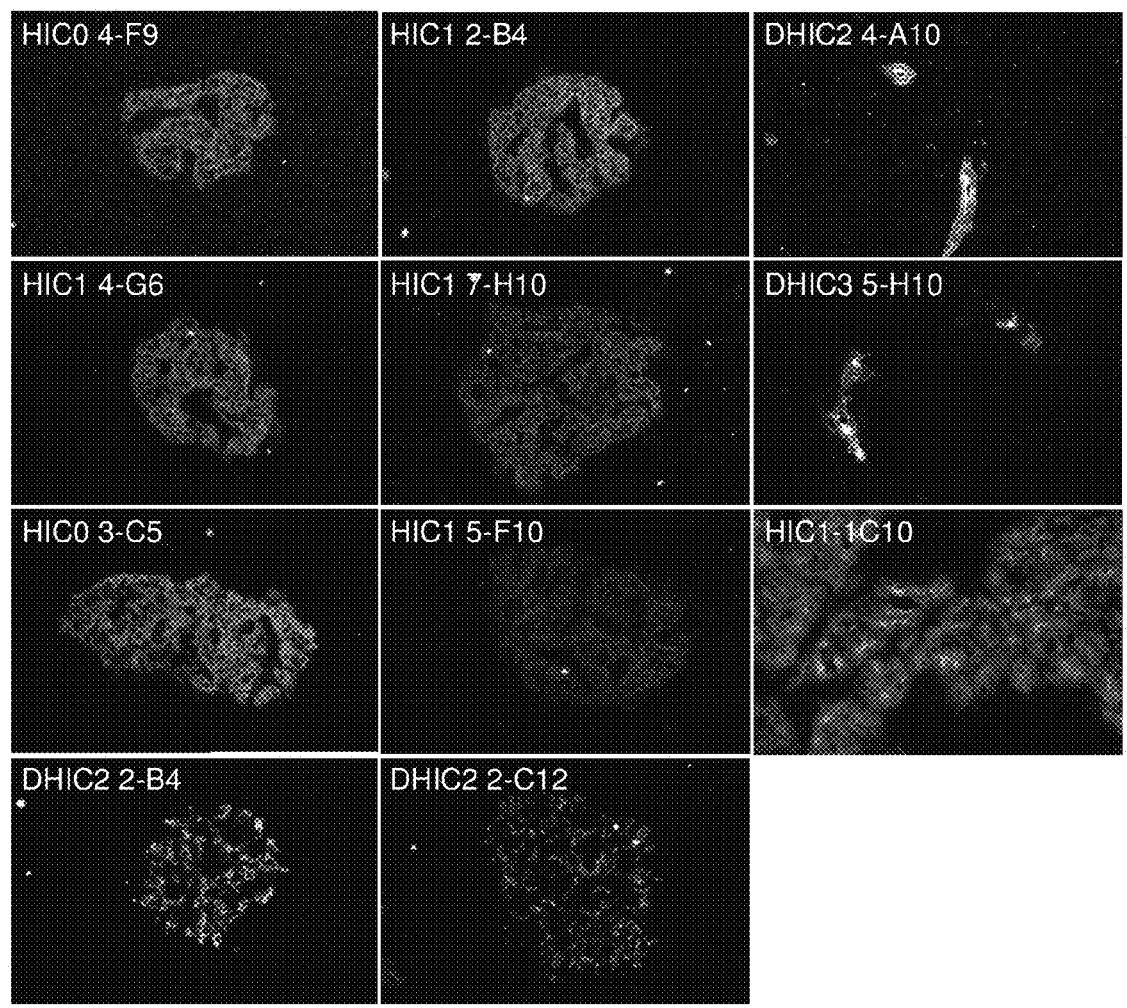
FIG. 1 is a set of digital images obtained using monoclonal antibodies directed against antigens associated with pancreatic cells. Each panel in this figure illustrates staining with antibody from an independently derived hybridoma. Panels HIC0 4-F9, HIC1 2-B4, HIC1 4-G6, HIC1 5-F10 and HIC1 7-H10 illustrate staining of all islet cells (pan-islet). The panel labeled HIC0 3-C5 illustrates staining with an antibody that binds to a subset of endocrine cells (including a subset of β cells). Panels labeled DHIC2 2-B4 and DHIC2 2-C12 illustrate staining with antibodies that react with alpha cells, although DHIC2 2-B4 likely reacts to a lesser extent with other pancreatic endocrine cells. Antibodies with duct-specific labeling are illustrated in panels DHIC2 4-A10 and DHIC3 5-H10, and exocrine acinar labeling is shown in panel HIC1 1-C10. Sections of pancreas were incubated with primary antibodies, then with a Cy-3-conjugated anti-mouse Ig (H+L) antibody. Cells reacting with primary antibody appear light against the dark background of cells that do not react with the antibody.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [899-71968-07_Sequence_Listing.txt, Jan. 20, 2011, 20.9 KB], which is incorporated by reference herein

DETAILED DESCRIPTION

I. Abbreviations
   CDR: complementarity determining region
   dsFv: disulfide stabilized fragment of a variable region
   DMEM: Dulbecco's modified eagle medium
   ELISA: enzyme-linked immunosorbent assay
   EM: effector molecule
   Fab': antigen binding immunoglobulin fragment
   $F(ab)'_2$: divalent antigen binding immunoglobulin fragment
   FACS: fluorescence activated cell sorting
   Fv: fragment of a variable region
   kDa: kilodaltons
   LCDR: light chain complementarity determining region
   HCDR: heavy chain complementarity determining region
   Ig: immunoglobulin
   MAb: monoclonal antibody
   PBS: phosphate buffered saline
   PP: pancreatic polypeptide scFv: single chain fragment of a variable region
SDR: specificity determining residues
SDS-PAGE: sodium dodecyl (lauryl) sulfate-polyacrylamide gel electrophoresis
RIA: radioimmunoas says
$V_H$: variable region of a heavy chain
$V_L$: variable region of a light chain II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

α cells: Mature glucagon producing cells. In vivo, these cells are found in the pancreatic islets of Langerhans.

β cells: Mature insulin producing cells. In vivo, these cells are found in the pancreatic islets of Langerhans, δ cells: Mature somatostatin producing cells. In vivo, these cells are found in the pancreatic islets of Langerhans.

PP cells: Mature pancreatic polypeptide (PP) producing cells. In vivo, these cells are found in the pancreatic islets of Langerhans.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and binds an epitope of an antigen or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (k). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest*, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds an antigen of interest has a specific $V_H$ region and the $V_L$ region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds a cell surface antigen on a pancreatic endocrine cell.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, such as at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Artificial Islets: Clusters of pancreatic endocrine cells formed by the differentiation of stem or progenitor cells including ES cell in vitro, dislodged clusters of pancreatic endocrine cells, endocrine cells differentiated from stem cells or progenitor cells including ES cells in vitro, cells that have undergone a mesenchymal-to-epithelial or epithelial-to-mesenchymal-to-epithelial transition or endocrine cells aggregated into a cluster in vitro.

Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In yet another embodiment, a high binding affinity is measured by a competition radioimmunoas say. In several examples, a high binding affinity is at least about $1 \times 10^{-8}$ M. In other embodiments, a high binding affinity is at least about $1.5 \times 10^{-8}$ M, at least about $2.0 \times 10^{-8}$ M, at least about $2.5 \times 10^{-8}$M, at least about $3.0 \times 10^{-8}$M, at least about $3.5 \times 10^{-8}$M, at least about $4.0 \times 10^{-8}$M, at least about $4.5 \times 10^{-8}$M, or at least about $5.0 \times 10^{-8}$ M.

Chimeric antibody: An antibody which includes sequences derived from two different antibodies, which typically are of different species. Most typically, chimeric antibodies include human and murine antibody domains, generally human constant regions and murine variable regions, murine CDRs and/or murine SDRs.

Complementarity Determining Region (CDR): Amino acid sequences which together define the binding affinity and specificity of the natural Fv region of a native Ig binding site. The light and heavy chains of an Ig each have three CDRs, designated L-CDR1, L-CDR2, L-CDR3 and H-CDR1, H-CDR2, H-CDR3, respectively. By definition, the CDRs of the light chain are bounded by the residues at positions 24 and 34 (L-CDR1), 50 and 56 (L-CDR2), 89 and 97 (L-CDR3); the CDRs of the heavy chain are bounded by the residues at positions 31 and 35b (H-CDR1), 50 and 65 (H-CDR2), 95 and 102 (H-CDR3), using the numbering convention delineated by Kabat et al., (1991) *Sequences of Proteins of Immunological Interest*, $5^{th}$ Edition, U.S. Department of Health and Human Services, Public Health Service, National Institutes of Health, Bethesda, Md. (NIH Publication No. 91-3242).

Contacting: Placement in direct physical association. Includes both in solid and liquid form.

Differentiation: The process whereby relatively unspecialized cells (e.g., embryonic cells) acquire specialized structural and/or functional features characteristic of mature cells. Similarly, "differentiate" refers to this process. Typically, during differentiation, cellular structure alters and tissue-specific proteins appear. The term "differentiated pancreatic endocrine cell" refers to cells expressing a protein characteristic of the specific pancreatic endocrine cell type. A differentiated pancreatic endocrine cell includes an α cell, a β cell, a δ cell, and a PP cell, which express glucagon, insulin, somatostatin, and pancreatic polypeptide, respectively.

Growth factor: A substance that promotes cell growth, survival, and/or differentiation. Growth factors include molecules that function as growth stimulators (mitogens), molecules that function as growth inhibitors (e.g. negative growth factors) factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation. Examples of growth factors are fibroblast growth factor (FGF)2, epidermal growth factor (EGF), ciliary neurotrophic factor (CNTF), hepatocyte growth factor (HGF), nerve growth factor (NGF), and actvin-A.

Effective amount or Therapeutically effective amount: The amount of agent or cells that is an amount sufficient to prevent, treat (including prophylaxis), reduce and/or ameliorate the symptoms and/or underlying causes of any of a disorder or disease. In one embodiment, an "effective amount" is sufficient to reduce or eliminate a symptom of a disease, such as a pancreatic cancer. In another embodiment, an effective amount is an amount sufficient to overcome the disease itself, such as in diabetes.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art. See, for example, U.S. Pat. No. 4,957,735; and Connor et al., *Pharm. Ther.* 28:341-365, 1985. Diagnostic agents or moieties include radioisotopes and other detectable labels. Detectable labels useful for such purposes are also well known in the art, and include radioactive isotopes such as $^{32}$P, $^{125}$I, and $^{131}$I, fluorophores, chemiluminescent agents, magnetic resonance imaging agents and enzymes.

Endocrine: Tissue which secretes regulatory hormones directly into the bloodstream without the need for an associated duct system.

Epitope: An antigenic determinant. These are particular chemical groups or peptide sequences on a molecule that are antigenic, i.e. that elicit a specific immune response. An antibody specifically binds a particular antigenic epitope on a polypeptide.

Epithelial-to-Mesenchymal Transition: The epithelium is the covering of internal and external surfaces of the body, including the lining of vessels and other small cavities that consists of cells joined by biological cementing substances. Generally, fully differentiated epithelial cells express proteins characteristic of a differentiated phenotype, such as insulin, and have a limited capacity to proliferate. The mesenchyme is the meshwork of loosely organized embryonic connective tissue in the mesoderm from which are formed the connective tissues of the body, along with the blood vessels and lymphatic vessels. An "epithelial-to-mesenchymal" transition is a biological process in which cells of an epithelial origin, such as pancreatic endocrine cells, adopt the characteristics of mesenchymal cells. A "mesenchymal-to-epithelial" transition is the reverse process, wherein mesencymal cells adopt characteristics of epithelial cells. An "epithelial-to-mesenchymal-to-epithelial" transition can occur when epithelial cells transiently adopt mesenchymal characteristics before resuming epithelial characteristics. These processes can be induced in cell culture.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells.

Expressed: Translation of a nucleic acid into a protein. Proteins may be expressed and remain intracellular, become a component of the cell surface membrane, or be secreted into the extracellular matrix or medium.

Exocrine: Secretory tissue which distributes its products, such as enzymes, via an associated duct network. The exocrine pancreas is the part of the pancreas that secretes enzymes required for digestion. The exocrine cells of the pancreas include the centroacinar cells and basophilic cells, which produce secretin and cholecystokinin.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework Region: Amino acid sequences interposed between CDRs. Includes variable light and variable heavy framework regions. The framework regions serve to hold the CDRs in an appropriate orientation for antigen binding.

Heterologous: A heterologous sequence is a sequence that is not normally (in the wild-type sequence) found adjacent to a second sequence. In one embodiment, the sequence is from a different genetic source, such as a virus or organism, than the second sequence.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (such as antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide.

Immunologically reactive conditions: Includes reference to conditions which allow an antibody raised against a particular epitope to bind to that epitope (or cell expressing the epitope) to a detectably greater degree than, and/or to the substantial exclusion of, binding to substantially all other epitopes (or cells not expressing the epitope). Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Islets of Langerhans: Small discrete clusters of pancreatic endocrine tissue. In vivo, in an adult mammal, the islets of Langerhans are found in the pancreas as discrete clusters (islands) of pancreatic endocrine tissue surrounded by the pancreatic exocrine (or acinar) tissue. In vivo, the islets of Langerhans consist of the α cells, β cells, δ cells, and PP cells. Histologically, the islets of Langerhans consist of a central core of β cells surrounded by an outer layer of α cells, δ cells, and PP cells. The islets of Langerhans are sometimes referred to herein as "islets."

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids. An isolated cell type has been substantially separated from other cell types, such as a different cell type that occurs in an organ. A purified cell or component can be at least 90%, at least 95%, at least 96%, at least 97%, at least 98%, or at least 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes.

Linker peptide: A peptide within an antibody binding fragment (such as an Fv fragment) which serves to indirectly bond the variable heavy chain to the variable light chain. "Linker" can also refer to a peptide serving to link a targeting moiety, such as a scFv, to an effector molecule, such as a cytotoxin or a detectable label.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule ("EM"). The linkage can be either by chemical or recombinant means. "Chemical means" refers to a reaction between the antibody moiety and the effector molecule such that there is a covalent bond formed between the two molecules to form one molecule.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=-4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Pancreatic endocrine cell: An endocrine cell of pancreatic origin that produces one or more pancreatic hormone, such as insulin, glucagon, somatostatin, or pancreatic polypeptide. Subsets of pancreatic endocrine cells include the α (glucagons producing), β (insulin producing) δ (somatostatin producing) or PP (pancreatic polypeptide producing) cells. Additional subsets produce more than one pancreatic hormone, such as, but not limited to, a cell that produces both insulin and glucagon, or a cell that produces insulin, glucagon, and somatostatin, or a cell that produces insulin and somatostatin.

Pancreatic cancer: A malignant tumor within the pancreas. The prognosis is generally poor. About 95% of pancreatic cancers are adenocarcinomas. The remaining 5% are tumors of the exocrine pancreas (for example, serous cystadenomas), ascinar cell cancers, and pancreatic neuroendocrine tumors (such as insulinomas). An "insulinoma" is a cancer of the beta cells that retains the ability to secrete insulin. Patients with insulinomas usually develop neuroglycopenic symptoms. These include recurrent headache, lethargy, diplopia, and blurred vision, particularly with exercise or fasting. Severe hypoglycemia may result in seizures, coma and permanent neurological damage. Symptoms resulting from the catecholaminergic response to hypoglycemia (for example, tremulousness, palpitations, tachycardia, sweating, hunger, anxiety, nausea). A pancreatic adenocarciona occurs in the glandular tissue. Symptoms include abdominal pain, loss of appetite, weight loss, jaundice and painless extension of the gallbladder.

Classical treatment for pancreatic cancer, including adenocarcinomas and insulinomas includes surgical resection (such as the Whipple procedure) and chemotherapy with agent such as fluorouracil, gemcitabine, and erlotinib.

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein is intended to encompass any amino acid sequence and include modified sequences such as glycoproteins. The term "polypeptide" is specifically intended to cover naturally occurring proteins, as well as those that are recombinantly or synthetically produced.

The term "polypeptide fragment" refers to a portion of a polypeptide which exhibits at least one useful epitope. The term "functional fragments of a polypeptide" refers to all fragments of a polypeptide that retain an activity of the polypeptide. Biologically functional fragments, for example, can vary in size from a polypeptide fragment as small as an epitope capable of binding an antibody molecule to a large polypeptide capable of participating in the characteristic induction or programming of phenotypic changes within a cell. An "epitope" is a region of a polypeptide capable of binding an immunoglobulin generated in response to contact with an antigen. Thus, smaller peptides containing the biological activity of insulin, or conservative variants of the insulin, are thus included as being of use.

The term "soluble" refers to a form of a polypeptide that is not inserted into a cell membrane.

The term "substantially purified polypeptide" as used herein refers to a polypeptide which is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative substitutions replace one amino acid with another amino acid that is similar in size, hydrophobicity, etc. Variations in the cDNA sequence that result in amino acid changes, whether conservative or not, should be minimized in order to preserve the functional and immunologic identity of the encoded protein. The immunologic identity of the protein may be assessed by determining if it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80, 90 or even 95% or 98% identical to the native amino acid sequence.

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or a composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Primers: Short nucleic acids, for example DNA oligonucleotides 10 nucleotides or more in length, which are annealed to a complementary target DNA strand by nucleic acid hybridization to form a hybrid between the primer and the target DNA strand, then extended along the target DNA strand by a DNA polymerase enzyme. Primer pairs can be used for amplification of a nucleic acid sequence, such as by the polymerase chain reaction (PCR) or other nucleic-acid amplification methods known in the art.

Probes and primers as used in the present invention may, for example, include at least 10 nucleotides of the nucleic acid sequences that are shown to encode specific proteins. In order to enhance specificity, longer probes and primers may also be employed, such as probes and primers that comprise 15, 20, 30, 40, 50, 60, 70, 80, 90 or 100 consecutive nucleotides of the disclosed nucleic acid sequences. Methods for preparing and using probes and primers are described in the references, for example Sambrook et al. (1989) Molecular Cloning: A Laboratory Manual, Cold Spring Harbor, N.Y.; Ausubel et al. (1987) Current Protocols in Molecular Biology, Greene Publ. Assoc. & Wiley-Intersciences; Innis et al. (1990) PCR Protocols, A Guide to Methods and Applications, Innis et al. (Eds.), Academic Press, San Diego, Calif. PCR primer pairs can be derived from a known sequence, for example, by using computer programs intended for that purpose such as Primer (Version 0.5, 1991, Whitehead Institute for Biomedical Research, Cambridge, Mass.).

When referring to a probe or primer, the term specific for (a target sequence) indicates that the probe or primer hybridizes under stringent conditions substantially only to the target sequence in a given sample comprising the target sequence.

Promoter: A promoter is an array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, such as by genetic engineering techniques. Similarly, a recombinant protein is one encoded for by a recombinant nucleic acid molecule.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (such as GC versus AT content), and nucleic acid type (such as RNA versus DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (see *Molecular Cloning: A Laboratory Manual*, 2nd ed., Vol. 1-3, ed. Sambrook et al., Cold Spring Harbor Laboratory Press, Cold Spring Harbor, N.Y., 1989). Washing can be carried out using only one of these conditions, for example, high stringency conditions, or each of the conditions can be used, for example, for 10-15 minutes each, in the order listed above, repeating any or all of the steps listed. However, as mentioned above, optimal conditions will vary, depending on the particular hybridization reaction involved, and can be determined empirically.

Sequence identity of amino acid sequences: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus a β cell specific binding agent is an agent that binds substantially to a β cell, and a pancreatic endocrine cell specific binding agent is an gent that binds substantially only to pancreatic endocrine cells or a subset thereof (and not to pancreatic exocrine cells). Similarly, a pancreatic exocrine cell specific binding agent is an agent that binds substantially to exocrine cells. In one embodiment, the specific binding agent is a monoclonal or polyclonal antibody that specifically binds a type of pancreatic cell.

The term "specifically binds" refers, with respect to a cell, such as a pancreatic endocrine cell, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue expressing the target epitope as compared to a cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Stem cell: A cell that can generate fully differentiated functional cells of more than one given cell type. The role of stem cells in vivo is to replace cells that are destroyed during the normal life of an animal. Generally, stem cells are pluripotent and can divide without limit. After division, the stem cell may remain as a stem cell, become a precursor cell, or proceed to terminal differentiation. Although appearing morphologically unspecialized, the stem cell may be considered differentiated where the possibilities for further differentiation are limited. An embryonic stem cell is one type of stem cell. A "tissue-specific stem cell" (an adult stem cell) is another type of stem cell, one that gives rise to cells of a specific tissue type. A precursor cell is a cell that can generate a fully differentiated functional cell of at least one given cell type. Precursor cells can divide, but have a limited ability to give rise to new precursor cells. A "pancreatic precursor cell" is a precursor cell that gives rise to one or more cell types within the pancreas. In one embodiment, a pancreatic endocrine precursor cell gives rise to all of the pancreatic endocrine cells (α cells, β cells, δ cells, and PP cells), but does not give rise to other cells, such as the pancreatic exocrine cells. In another embodiment, a pancreatic precursor cell gives rise to more than one type of pancreatic endocrine cell, although it may not give rise to all of the types of endocrine cells. One specific, non-limiting example of a pancreatic precursor cell is a β precursor cell that give rise to both differentiated α and β cells.

Subject: Any mammal, such as humans, non-human primates, pigs, sheep, cows, rodents and the like which is to be the recipient of the particular treatment. In two non-limiting examples, a subject is a human subject or a murine subject.

T Cell: A white blood cell critical to the immune response. T cells include, but are not limited to, CD4$^+$ T cells and CD8$^+$ T cells. A CD4$^+$ T lymphocyte is an immune cell that carries a marker on its surface known as "cluster of differentiation 4" (CD4). These cells, also known as helper T cells, help orchestrate the immune response, including antibody responses as well as killer T cell responses. CD8$^+$ T cells carry the "cluster of differentiation 8" (CD8) marker. In one embodiment, CD8 T cells are cytotoxic T lymphocytes. In another embodiment, a CD8 cell is a suppressor T cell.

Therapeutic agent: Used in a generic sense, it includes treating agents, prophylactic agents, and replacement agents. A therapeutic agent can be an antibody that specifically binds pancreatic endocrine cells or a subset thereof.

Transduced and Transformed: A virus or vector "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transfection are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA. Methods for the introduction of genes into the pancreatic endocrine cells are known (e.g. see U.S. Pat. No. 6,110,743, herein incorporated by reference). These methods can be used to transduce a pancreatic endocrine cell produced by the methods described herein, or an artificial islet produced by the methods described herein.

Genetic modification of the target cell is an indicium of successful transfection. "Genetically modified cells" refers to cells whose genotypes have been altered as a result of cellular uptakes of exogenous nucleotide sequence by transfection. A reference to a transfected cell or a genetically modified cell includes both the particular cell into which a vector or polynucleotide is introduced and progeny of that cell.

Transgene: An exogenous gene supplied by a vector.

Vector: A nucleic acid molecule as introduced into a host cell, thereby producing a transformed host cell. A vector may include nucleic acid sequences that permit it to replicate in the host cell, such as an origin of replication. A vector may also include one or more therapeutic genes and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Monoclonal Antibodies that Bind Pancreatic Cell Surface Antigens

Isolated monoclonal antibodies are disclosed herein that specifically bind cell surface antigens on a human pancreatic endocrine cell, a human pancreatic endocrine cell precursor, or both. The antibody can bind all types of pancreatic endocrine cells, or a subset thereof. In one example, the monoclonal antibody binds antigens on the cell surface of pancreatic endocrine cells (or a subset thereof) of an adult human. In another example, the monoclonal antibody binds a cell surface antigen expressed on an islet of Langerhans, either from an adult human or from a fetus. In one embodiment, the antibodies do not bind a pancreatic endocrine hormone, such as insulin, glucagon, somatostatin or pancreatic polypeptide, or their receptors. In a further embodiment, the monoclonal antibodies that specifically bind pancreatic endocrine cells (or a subset thereof) do not bind pancreatic exocrine cells and/or pancreatic ductal cells. In some examples, the antibodies specifically bind human pancreatic endocrine cells. In additional examples the antibodies specifically bind human pancreatic endocrine cells and specifically bind pancreatic endocrine cells of a non-human primate. These antibodies do not bind pancreatic exocrine cells.

In one example, the isolated monoclonal antibodies bind insulin-producing cell (β cells) or a subset of these cells. In additional examples, the isolated monoclonal antibodies bind a cell surface antigen that is expressed on the cell surface of one or more of insulin producing cells, somatostatin producing cells, pancreatic polypeptide producing cells and glucagon producing cells. In further examples, the monoclonal antibody binds glucagon producing cells, or glucagon producing cells and insulin producing cells. In an additional example, the antibody binds all types of pancreatic endocrine cells (insulin, glucagon, somatostatin, and pancreatic polypeptide producing pancreatic endocrine cells).

Also disclosed herein are isolated monoclonal antibodies that bind cell surface antigens that are specific to pancreatic exocrine cells or pancreatic ductal cells. In one example, the monoclonal antibody specifically binds antigens on the cell surface of pancreatic exocrine cells (or a subset thereof) of an adult human and/or a fetus. In another example, the monoclonal antibody specifically binds a cell surface antigen expressed on a pancreatic ductal cell, either from an adult human or from a fetus. In one embodiment, the antibodies that specifically bind a pancreatic ductal cell or a pancreatic exocrine cell do not specifically bind pancreatic endocrine cells, such as cells that produce insulin, glucagon, somatostatin or pancreatic polypeptide. In some examples, the antibodies specifically bind human pancreatic exocrine cells, and do not bind pancreatic endocrine cells or pancreatic ductal cells. In additional examples, the antibodies specifically bind human pancreatic ductal cells, but do not bind pancreatic exocrine cells or pancreatic ductal cells.

Generally, the monoclonal antibodies each include a variable heavy ($V_H$) and a variable light ($V_L$) chain and specifically bind the cell surface antigen. For example, the antibody can specifically bind pancreatic endocrine cells, and can bind the cell surface antigen of endocrine cells with an affinity constant of at least $10^6$ $M^{-1}$, such as at least $10^7$ $M^{-1}$, at least $10^8$ $M^{-1}$, at least $5\times10^8$ $M^{-1}$, or at least $10^9$ $M^{-1}$. In a second example, the antibody can specifically bind pancreatic exocrine cells, and can bind the cell surface antigen of exocrine cells with an affinity constant of at least $10^6$ $M^{-1}$, such as at least $10^7$ $M^{-1}$, at least $10^8$ $M^{-1}$, at least $5\times10^8$ $M^{-1}$, or at least $10^9$ $M^{-1}$. In a third example, the antibody can specifically bind pancreatic ductal cells, and can bind the cell surface antigen of ductal cells with an affinity constant of at least $10^6$ $M^{-1}$, such as at least $10^7$ $M^{-1}$, at least $10^8$ $M^{-1}$, at least $5\times10^8$ $M^{-1}$, or at least $10^9$ $M^{-1}$.

It should be noted that antibody fragments are encompassed by the present disclosure. Thus the isolated monoclonal antibody can be, for example, a Fab' fragment, a F(ab)'$_2$ fragment, a single chain Fv protein ("scFv"), or a disulfide stabilized Fv protein ("dsFv").

Monoclonal antibodies that specifically bind pancreatic endocrine cells or a subset thereof can bind the antigen recognized by an antibody produced by one or more of hybridomas HIC04-F9, HIC1 2-B4, HIC1 4-G6, HIC1 7-H10, HIC03-05, HIC1 5-F10, DHIC2 2-B4, or DHIC2 2-C12. Patent deposits of hybridomas HIC03-05, HIC0 4-F9, DHIC2 2-B4 and DHIC 2-C12, HIC1 5-F10, HIC1 7-H10, HIC1 2-B4 and HIC 1 4-G6 were made with the American Type Culture Collection (ATCC), 10801 University Blvd, Manassas, Va. 20110-2209 on Apr. 27, 2006, in accordance with the Budapest Treaty (Accession Nos. PTA-7556, PTA-7557, PTA-7558, PTA-7559, PTA-7560, PTA-7561, PTA-7562 and PTA-7563, respectively). It should be noted that a "monoclonal antibody produced by one or more hybridomas" refers to antibodies produced by the hybridoma or any progeny thereof.

In several embodiments, the heavy chain of the variable region of the monoclonal antibody includes one or more of the following CDR sequences.

TABLE 1

|  | CDR 1 | CDR 2 | CDR 3 |
|---|---|---|---|
| HIC0 4-F9 | DYYIH (SEQ ID NO: 1) | WIDPENGNTIYDPKFQD (SEQ ID NO: 2) | YYGSTYYFDY (SEQ ID NO: 3) |
| HIC0 5-F10 | EYI IH (SEQ ID NO: 4) | WFYPGSGGLKYSEKFKD (SEQ ID NO: 5) | HEKYFDY (SEQ ID NO: 6) |
| HIC0 3-C5 | NYAMS (SEQ ID NO: 7) | TISSGGSYTYYPDSVKG (SEQ ID NO: 8) | QGDNYWYFDV (SEQ ID NO: 9) |
| HIC1 4-G6 | DYYMH (SEQ ID NO: 10) | FIRNKANGYTTEYSASVG (SEQ ID NO: 11) | DIKGDY (SEQ ID NO: 12) |
| HIC1 7-H10 | SYDMS (SEQ ID NO: 13) | YISSGGGSTYFPNTVKG (SEQ ID NO: 14) | HGGNQPWFAY (SEQ ID NO: 15) |
| DHIC2 2-C12 | TDYSMH (SED ID NO:35) | NTETGEPTYADDFKG (SEQ ID NO: 36) | GYGSSSWFAY (SEQ ID NO: 37) |

In additional embodiment, the antibody includes a heavy chain comprising the amino acid sequences listed in Table 2, or an amino acid sequence at least 95%, 96%, 97%, 98% or 99% identical to one of these sequences.

TABLE 2*

| Hybridoma ID | Full heavy chain V-region sequence |
|---|---|
| HIC0 4-F9 | EVQLQQSGAELVRPGALVKLSCKASGFNIK<u>DYYIHWVK</u> QKPEQGLEWIG<u>WIDPENGNTIYDPKFQ</u>DKASITSDTSS NTAYLQLSSLTSEDTAVYYCTS<u>YYGSTYYFDY</u>WGQGT (SEQ ID NO: 39) |
| HIC0 3-C5 | EVMLVESGGGLVKPGGSLKLSCAASGFTF<u>SNYAMS</u>WVR QTPEKRLEWVA<u>TISSGGSYTYYPDSVK</u>GRFTISRDNAK NTLYLQMSSLRSEDTAMYYCAR<u>QGDNYWYFDV</u>WGAGTT VTVSSESQ (SEQ ID NO: 16) |
| HIC1 5-F10 | VQLQQSGAELVKPGASVKLSCKASGYTFT<u>EYIIH</u>WVKQ RSGQGLEWIG<u>WFYPGSGGLKYSEKFK</u>DKATLTADKSSS TVYMELSRLTSEDSAVYFCAR<u>HEKYFDY</u>WGQGTT (SEQ ID NO: 17) |
| HIC1 4-G6 | EVKLVESGGGLVQPGGSLRLSCATSGFTFT<u>DYYMH</u>WVR QPPGKALEWLG<u>FIRNKANGYTTEYSASVK</u>GRFTISRDN SQSILYLQMNTLRAEDSATYYCTR<u>DIKGDY</u>WGQGTS (SEQ ID NO: 18) |
| HIC1 7-H10 | EVQLVESGGGLVKPGGSLKLSCAASGFAFS<u>SYDMS</u>WVR QAPDKRLEWVA<u>YISSGGGSTYFPNTVK</u>GRFTISRDNAK NTLSLQMSSLRSEDTAMYYCTR<u>HGGNQPWFAY</u>WGQGT (SEQ ID NO: 19) |
| DHIC2 2-C12 | QVQIQLVQSGPELKKPGETVKISCKASGYTFT<u>DYSMH</u>W VKQAPGKGLKWMG<u>WINTETGEPTYADDFK</u>GRFAFSLET SASTAYLQINNLKNEDTATYFCSR<u>GYGSSSWFAY</u>WGQG TLVT (SEQ ID NO: 38) |

*CDR amino acid sequences are underlined.

In several embodiments, the antibody includes a heavy chain comprising one of the CDRs listed in Table 1, or a combination of these CDRs. One specific example is an antibody including a heavy chain comprising SEQ ID NO: 1, SEQ ID NO: 2, SEQ ID NO: 3 or a combination thereof. In additional examples the antibody includes a heavy chain comprising SEQ ID NO: 4, SEQ ID NO: 5, SEQ ID NO: 6 or a combination thereof. In further examples, the antibody includes a heavy chain comprising SEQ ID NO: 7, SEQ ID NO: 8, SEQ ID NO: 9 or a combination thereof. In yet another example, the antibody includes a heavy chain comprising SEQ ID NO: 10, SEQ ID NO: 11, SEQ ID NO: 12, or a combination thereof. In another example, the antibody includes a heavy chain comprising SEQ ID NO: 13, SEQ ID NO: 14, SEQ ID NO: 15 or a combination thereof. The antibody can include a heavy chain comprising at least one of SEQ ID NOs: 1-15, wherein the antibody specifically binds pancreatic endocrine cells, or a subset thereof.

In several embodiments the antibody includes a $V_H$ polypeptide including amino acid sequences of CDRs that are at least about 90% identical, such as at least about 95%, at least about 98%, or at least about 99% identical to the amino acid sequence set forth as SEQ ID NO: 1, SEQ ID NO: 2 and SEQ ID NO: 3, or amino acid sequences of CDRs that are at least about 90% identical, such as at least about 95%, at least about 98%, or at least about 99% identical to the amino acid sequence set forth as SEQ ID NO: 4, SEQ ID NO: 5 and SEQ ID NO: 6, or a $V_H$ polypeptide having amino acid sequences of the CDRs that are at least about 90% identical, such as at least about 95%, at least about 98%, or at least about 99% identical to the amino acid sequence set forth as SEQ ID NO: 7, SEQ ID NO: 8 and SEQ ID NO: 9. In additional embodiments the antibody includes a $V_H$ polypeptide including amino acid sequences of CDRs that are at least about 90% identical, such as at least about 95%, at least about 98%, or at least about 99% identical to the amino acid sequence set forth as SEQ ID NO: 10, SEQ ID NO: 11 and SEQ ID NO: 12, or amino acid sequences of CDRs that are at least about 90% identical, such as at least about 95%, at least about 98%, or at least about 99% identical to the amino acid sequence set forth as SEQ ID NO: 13, SEQ ID NO: 14 and SEQ ID NO: 15. In a further embodiment, the antibody includes $V_H$ polypeptide including an amino acid sequence set forth as one of SEQ ID NOs: 16-18 and 38-39 (see also FIG. 3).

In additional embodiment, the antibody includes the CDR sequences from monoclonal antibodies that specifically bind the pancreatic endocrine cell antigen recognized by an antibody secreted by the hybridoma HIC0 4-F9, HIC1 2-B4, HIC1 4-G6, HIC1 7-H10, HIC0 3-C5, HIC1 5-F10, DHIC2 2-B4, or DHIC2 2-C12. Patent deposits of hybridomas HIC0 3-C5, HIC0 4-F9, DHIC2 2-B4 and DHIC 2-C12, HIC1 5-F10, HIC1 7-H10, HIC1 2-B4 and HIC1 4-G6 were made with the ATCC on Apr. 27, 2006, in accordance with the Budapest Treaty (Accession Nos. PTA-7556, PTA-7557, PTA-7558, PTA-7559, PTA-7560, PTA-7561, PTA-7562 and PTA-7563, respectively). The framework region included in the antibody that binds pancreatic endocrine cells (or a subset thereof) can be the endogenous framework region (from monoclonal antibodies produced by HIC0 4-F9, HIC1 2-B4, HIC1 4-G6, HIC1 7-H10, HIC0 3-C5, HIC1 5-F10, DHIC2 2-B4, or DHIC2 2-C12, respectively). Alternatively, a heterologous framework region, such as, but not limited to a human framework region, can be included in the heavy and/or light chain of the antibodies.

In yet another embodiment the monoclonal antibody specifically binds ductal cells, such as an antibody secreted by DHIC2 4-A10 or DHIC3 5-H10. These hybridomas were deposited with the ATCC in accordance with the Budapest Treaty on Apr. 26, 2007. It should be noted that a "monoclonal antibody produced by one or more of hybridomas DHIC2 4-A10 or DHIC3 5-H10" refers to antibodies produced by these hybridomas or any progeny thereof.

Thus, the antibody that specifically binds pancreatic ductal cells can include the CDR sequences from monoclonal antibodies that specifically bind the ductal cell surface antigen secreted by the hybridoma DHIC2 4-A10 or DHIC3 5-H10. The framework region included in the antibody that binds pancreatic endocrine cells (or a subset thereof) can be the endogenous framework region (from monoclonal antibodies produced by DHIC2 4-A10 or DHIC3 5-H10 respectively). Alternatively, a heterologous framework region, such as, but not limited to a human framework region, can be included in the heavy and/or light chain of the antibodies.

In a further embodiment the monoclonal antibody specifically binds exocrine cells, such as the antibody secreted by HIC1 1-C10. This hybridoma was deposited with ATCC in accordance with the Budapest Treaty on Apr. 26, 2007. It should be noted that a "monoclonal antibody produced by the hybridom HIC1 1-C10" refers to antibodies produced by these hybridomas or any progeny thereof.

Thus, the antibody that specifically binds pancreatic exocrine cells can include the CDR sequences from monocolanal antibodies that specifically bind the exocrine cells surface antigen secreted by the hybridoma HIC1 1-C 10. The framework region included in the antibody that binds pancreatic endocrine cells (or a subset thereof) can be the endogenous framework region (from monoclonal antibodies produced by HIC1 1-C10). Alternatively, a heterologous framework region, such as, but not limited to a human framework region, can be included in the heavy and/or light chain of the antibodies.

In one example the sequence of the specificity determining regions of each CDR (from any of the antibodies disclosed herein) is determined. Residues outside the SDR (non-ligand contacting sites) can be substituted and the monoclonal antibody retains its ability to bind pancreatic endocrine cells. For example, in any of the CDR sequences as in the table above, at most one, two or three amino acids are substituted.

The production of chimeric antibodies, which include a framework region from one antibody and the CDRs from a different antibody, is well known in the art. For example, humanized antibodies can be routinely produced. The antibody or antibody fragment can be a humanized immunoglobulin having complementarity determining regions (CDRs) from a donor monoclonal antibody that binds a cell surface antigen of pancreatic cells (such as endocrine, exocrine or ductal cells) and immunoglobulin and heavy and light chain variable region frameworks from human acceptor immunoglobulin heavy and light chain frameworks. Generally, the humanized immunoglobulin specifically binds to the cell surface antigen (or cells expressing the antigen) with an affinity constant of at least $10^7$ $M^{-1}$, such as at least $10^8$ $M^{-1}$ at least $5 \times 10^8$ $M^{-1}$ or at least $10^9$ $M^{-1}$.

Humanized monoclonal antibodies can be produced by transferring donor complementarity determining regions (CDRs) from heavy and light variable chains of the donor mouse immunoglobulin. In one example, the CDRs from the monoclonal antibodies produced by the hybridomas HIC0 4-F9, HIC1 2-B4, HIC1 4-G6, HIC1 7-H10, HIC03-05, HIC1 5-F10, DHIC2 2-B4, or DHIC2 2-C12 are transferred into a human variable domain, and then substituting human residues in the framework regions when required to retain affinity. In another example, the CDRs from the monoclonal antibodies produced by the hybridomas DHIC2 4-A10 or DHIC3 5-H10 are transferred into a human variable domain, and then substituting human residues in the framework regions when required to retain affinity. In a further example, the CDRs from the monoclonal antibody produced by the hybridoma HIC1 1-C10 are transferred into a human variable domain, and then substituting human residues in the framework regions when required to retain affinity.

The use of antibody components derived from humanized monoclonal antibodies obviates potential problems associated with the immunogenicity of the constant regions of the donor antibody. Techniques for producing humanized monoclonal antibodies are described, for example, by Jones et al., Nature 321:522, 1986; Riechmann et al., Nature 332:323, 1988; Verhoeyen et al., Science 239:1534, 1988; Carter et al., Proc. Natl. Acad. Sci. U.S.A. 89:4285, 1992; Sandhu, Crit. Rev. Biotech. 12:437, 1992; and Singer et al., J. Immunol. 150:2844, 1993. The antibody may be of any isotype, but in several embodiments the antibody is an IgM or an IgG, including but not limited to, $IgG_1$, $IgG_2$, $IgG_3$ and $IgG_4$.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 95%, or at least about 99% identical to the sequence of the donor murine immunoglobulin heavy chain variable region framework. Human framework regions, and mutations that can be made in a humanized antibody framework regions, are known in the art (see, for example, in U.S. Pat. No. 5,585,089, which is incorporated herein by reference). One of skill in the art can readily select a human framework region of use.

Figure 3:
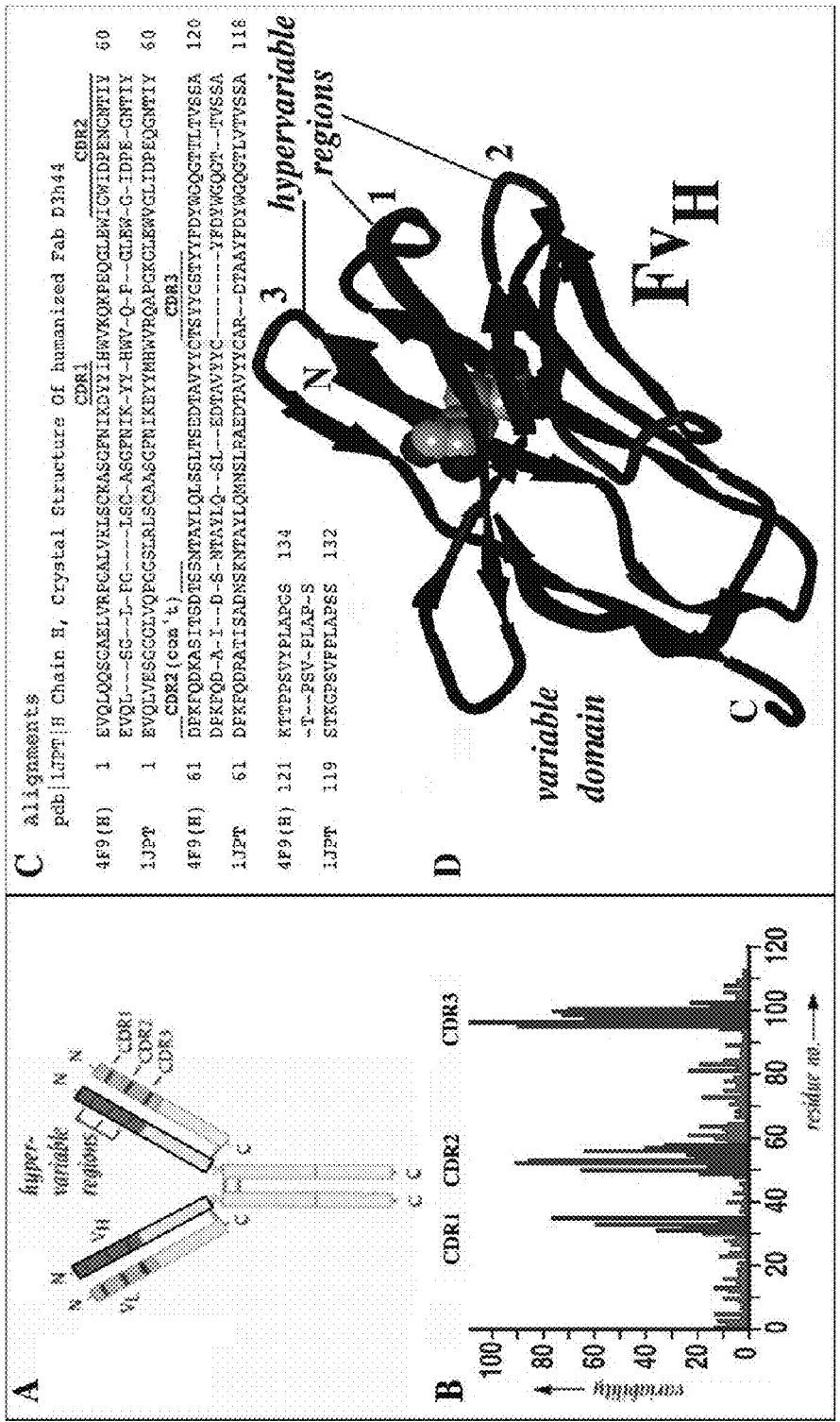
FIGS. 3A-3D are diagrams showing the production of humanized antibodies.
Figure 4:
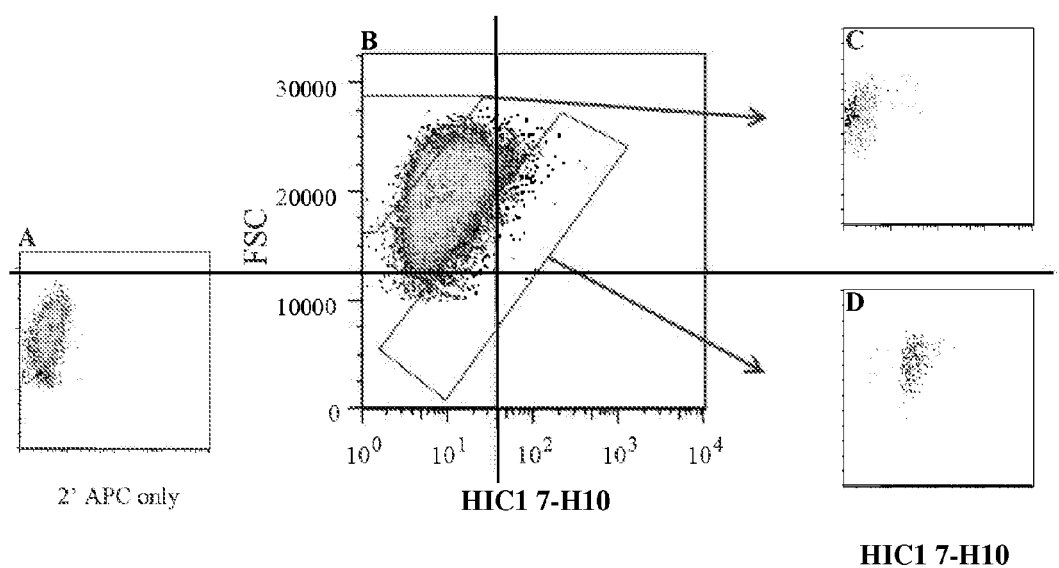
FIG. 4 is a plot of a FACS analysis that illustrates the separation of cells from an islet culture by FACS on the basis of their level of binding by HIC1 7-H10.

Exemplary human antibodies are shown in FIG. 3; additional exemplary human antibodies are LEN and 21/28 CL. The sequences of the heavy and light chain frameworks are known in the art. Exemplary light chain frameworks of human MAb LEN have the following sequences:

```
FR1: DIVMTQS PDSLAVSLGERATINC        (SEQ ID NO: 20)

FR2: WYQQKPGQPPLLIY                   (SEQ ID NO: 21)

FR3: GVPDRPFGSGSGTDFTLTISSLQAEDVAVYYC (SEQ ID NO: 22)

FR4: FGQGQTKLEIK                     (SEQ ID NO: 23)
```

Exemplary heavy chain frameworks of human MAb 21/28' CL have the following sequences:

```
FR1: QVQLVQSGAEVKKPQASVKVSCKASQYTFT   (SEQ ID NO: 24)

FR2: WVRQAPGQRLEWMG                   (SEQ ID NO: 25)

FR3: RVTITRDTSASTAYMELSSLRSEDTAVYYCAR (SEQ ID NO: 26)

FR4: WGQGTLVTVSS.                     (SEQ ID NO: 27)
```

These framework sequences are provided for example only; a humanized antibody can include the human framework region from any human monoclonal antibody of interest. In one example, the human framework region includes the amino acid sequence set forth as SEQ ID NO: 40 (see FIG. 3C).

Antibodies, such as murine monoclonal antibodies, chimeric antibodies, and humanized antibodies, include full length molecules as well as fragments thereof, such as Fab, F(ab')$_2$, and Fv which include a heavy chain and light chain variable region and are capable of binding the epitopic determinant on pancreatic endocrine cells or a subset thereof, pancreatic exocrine cells, or pancreatic ductal cells. These antibody fragments retain some ability to selectively bind with their antigen or receptor. These fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of an scFV. This has also been termed a "minianti-body."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of the monoclonal antibody produced by the hybridoma HIC0 4-F9, HIC1 2-B4, HIC1 4-G6, HIC1 7-H10, HIC0 3-C5, HIC1 5-F10, DHIC2 2-B4, or DHIC2 2-C12 (deposited in accordance with the Budapest treaty on Apr. 27, 2006) or a progeny thereof. In one group of embodiments, the antibodies have V$_H$ CDRs having the amino acid sequences shown above in Table 1, or a combination of these CDRs, as discussed above. In another group of embodiments, the antibodies have VH and VL CDRs from one of the monoclonal antibodies produced by the hybridomas HIC0 4-F9, HIC1 2-B4, HIC1 4-G6, HIC1 7-H10, HIC0 3-C5, HIC1 5-F10, DHIC2 2-B4, or DHIC2 2-C12 or a progeny thereof. Patent deposits of hybridomas HIC03-05, HIC0 4-F9, DHIC2 2-B4 and DHIC 2-C12, HIC1 5-F10, HIC1 7-H10, HIC1 2-B4 and HIC1 4-G6 were made with the ATCC on Apr. 27, 2006, in accordance with the Budapest Treaty (Accession Nos. PTA-7556, PTA-7557, PTA-7558, PTA-7559, PTA-7560, PTA-7561, PTA-7562 and PTA-7563, respectively. In a further group of embodiments, the antibodies have VH and VL CDRs from one of the monoclonal antibodies produced by the hybridomas DHIC2 4-A10, DHIC3 5-H10 OR HIC1 1-C10 (deposited in accordance with the Budapest Treaty on Apr. 26, 2007) or a progeny thereof.

In a further group of embodiments, the antibodies are Fv antibodies, which are typically about 25 kDa and contain a complete antigen-binding site with three CDRs per each heavy chain and each light chain. To produce these antibodies, the V$_H$ and the V$_L$ can be expressed from two individual nucleic acid constructs in a host cell. If the V$_H$ and the V$_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise V$_H$ and V$_L$ chains connected by a peptide linker. These single-chain antigen binding proteins (scFv) are prepared by constructing a structural gene comprising DNA sequences encoding the V$_H$ and V$_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Thus, one of skill in the art can readily review the sequences shown in Table 1, identify a conservative substitution, and produce the conservative variant using well-known molecular techniques.

Effector molecules, such as therapeutic, diagnostic, or detection moieties can be linked to an antibody of interest, such as an antibody that specifically binds a cell surface antigen on human pancreatic endocrine cells or a subset thereof, an antibody that specifically binds a cell surface antigen on a pancreatic exocrine cell, or an antibody that specifically binds a cell surface antigen on a pancreatic ductal cell, using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. When the target site is a tumor, a linker which is cleavable under conditions present at the tumor site (for example, when exposed to tumor-associated enzymes or acidic pH) may be used.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

Therapeutic agents include various drugs such as vinblastine, daunomycin and the like, and effector molecules such as cytotoxins including but not limited to native or modified *Pseudomonas* exotoxin or Diphtheria toxin, encapsulating agents, (such as liposomes) which themselves contain pharmacological compositions, target moieties and ligands. The choice of a particular therapeutic agent depends on the particular target molecule or cell and the biological effect desired to be evoked. Thus, for example, the therapeutic agent may be an effector molecule that is a cytotoxin which is used to bring about the death of a particular target cell, such as a pancreatic endocrine cells tumor (such as an insulinoma or glucagonoma). Conversely, where a non-lethal biological response is desired, a therapeutic agent can be conjugated to a non-lethal pharmacological agent or a liposome containing a non-lethal pharmacological agent.

Toxins can be employed with antibodies that specifically bind a cell surface antigen of a human pancreatic endocrine cells or a subset thereof, and fragments of these antibodies, for example, a svFv or a dsFv, to yield chimeric molecules, which are of use as immunotoxins. Exemplary toxins include *Pseudomonas* exotoxin (PE), ricin, abrin, diphtheria toxin and subunits thereof, ribotoxin, ribonuclease, saporin, gelonin and calicheamicin, as well as botulinum toxins A through F. These toxins are well known in the art and many are readily available from commercial sources (for example, Sigma Chemical Company, St. Louis, Mo.). These antibodies are of use, for example, for the treatment of tumors of pancreatic endocrine cells, such as insulinomas.

Diphtheria toxin is isolated from *Corynebacterium diphtheriae*. Typically, diphtheria toxin for use in immunotoxins is mutated to reduce or to eliminate non-specific toxicity. A mutant known as CRM 107, which has full enzymatic activity but markedly reduced non-specific toxicity, has been known since the 1970's (Laird and Groman, *J. Virol.* 19:220, 1976), and has been used in human clinical trials. See, U.S. Pat. No. 5,792,458 and U.S. Pat. No. 5,208,021.

Ricin is the lectin RCA60 from *Ricinus communis* (Castor bean). For examples of ricin, see, U.S. Pat. No. 5,079,163 and U.S. Pat. No. 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, *J. Biochim. Biophys. Acta* 266:543, 1972). The A chain is responsible for inactivating protein synthesis and killing cells. The B chain binds ricin to cell-surface galactose residues and facilitates transport of the A chain into the cytosol (Olsnes et al., *Nature* 249:627-631, 1974 and U.S. Pat. No. 3,060,165).

Ribonucleases have also been conjugated to targeting molecules for use as immunotoxins (see Suzuki et al., *Nat. Biotech.* 17:265-70, 1999). Exemplary ribotoxins such as α-sarcin and restrictocin are discussed in, for example Rathore et al., *Gene* 190:31-5, 1997; and Goyal and Batra, *Biochem.* 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., *J. Antibiot.* 42:1070-87, 1989). The drug is the toxic moiety of an immunotoxin in clinical trials (see, for example, Gillespie et al., *Ann. Oncol.* 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., *Agr. Biol. Chem.* 52:1095, 1988; and Olsnes, *Methods Enzymol.* 50:330-335, 1978).

In one embodiment, the toxin is *Pseudomonas* exotoxin (PE). Native *Pseudomonas* exotoxin A ("PE") is an extremely active monomeric protein (molecular weight 66 kD), secreted by *Pseudomonas aeruginosa*, which inhibits protein synthesis in eukaryotic cells. The native PE sequence and the sequence of modified PE are provided in U.S. Pat. No. 5,602,095, incorporated herein by reference. In one embodiment, native PE has a sequence set forth as:

```
                                          (SEQ ID NO: 28)
AEEAFDLWNE CAKACVLDLK DGVRSSRMSV DPAIADTNGQ

GVLHYSMVLE GGNDALKLAI DNALSITSDG LTIRLEGGVE

PNKPVRYSYT RQARGSWSLN WLVPIGHEKP SNIKVFIHEL

NAGNQLSHMS PIYTIEMGDE LLAKLARDAT FFVRAHESNE

MQPTLAISHA GVSVVMAQTQ PRREKRWSEW ASGKVLCLLD

PLDGVYNYLA QQRCNLDDTW EGKIYRVLAG NPAKHDLDIK

PTVISHRLHF PEGGSLAALT AHQACHLPLE TFTRHRQPRG

WEQLEQCGYP VQRLVALYLA ARLSWNQVDQ VIRNALASPG

SGGDLGEAIR EQPEQARLAL TLAAAESERF VRQGTGNDEA

GAANADVVSL TCPVAAGECA GPADSGDALL ERNYPTGAEF

LGDGGDVSFS TRGTQNWTVE RLLQAHRQLE ERGYVFVGYH

GTFLEAAQSI VFGGVRARSQ DLDAIWRGFY IAGDPALAYG

YAQDQEPDAR GRIRNGALLR VYVPRSSLPG FYRTSLTLAA

PEAAGEVERL IGHPLPLRLD AITGPEEEGG RLETILGWPL

AERTVVIPSA IPTDPRNVGG DLDPSSIPDK EQAISALPDY

ASQPGKPPRE DLK
```

Thus, the PE used in the immunotoxins disclosed herein includes the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell (such as a protein or pre-protein). Cytotoxic fragments of PE known in the art include PE40, PE38, and PE35. In several embodiments, the PE has been modified to reduce or eliminate non-specific cell binding, typically by deleting domain Ia, as taught in U.S. Pat. No. 4,892,827. U.S. Pat. No. 5,512,658, for instance, discloses that a mutated PE in which Domain Ia is present but in which the basic residues of domain Ia at positions 57, 246, 247, and 249 are replaced with acidic residues (glutamic acid, or "E") exhibits greatly diminished non-specific cytotoxicity. PE40 is a truncated derivative of PE (see, Pai et al., *Proc. Natl. Acad. Sci. USA* 88:3358-62, 1991; and Kondo et al., *J. Biol. Chem.* 263:9470-9475, 1988).

The antibodies or antibody fragments disclosed herein can be derivatized or linked to another molecule (such as another peptide or protein). In general, the antibodies or portion thereof is derivatized such that the binding to pancreatic endocrine cells is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

An antibody that binds pancreatic endocrine cells or a subset thereof, pancreatic exocrine cells or a subset thereof, or pancreatic ductal cells or a subset thereof, can also be labeled. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as Green fluorescent protein (GFP), Yellow fluorescent protein (YFP) and enhanced variants of these proteins. An antibody can also be labeled with enzymes that are useful for detection, such as horseradish peroxidase, β-galactosidase, luciferase, alkaline phosphatase, glucose oxidase and the like. When an antibody is labeled with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a paramagnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce steric hindrance.

An antibody can also be labeled with a radiolabeled amino acid. The radiolabel may be used for both diagnostic and therapeutic purposes. For instance, the radiolabel may be used to detect pancreatic endocrine cells or a subset thereof, pancreatic exocrine cells or a subset thereof, pancreatic ductal cells or a subset thereof, or a pancreatic tumor, by x-ray or other diagnostic techniques. Further, the radiolabel may be used therapeutically as a toxin for islet cell tumors or a pancreatic adenocarcinoma. Examples of labels for polypeptides include, but are not limited to, the following radioisotopes or radionuclides: $^3$H, $^{14}$C, and $^{125}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Nucleic acids encoding the amino acid sequences of the antibodies that bind pancreatic endocrine cells or a subset thereof are also provided herein. Nucleic acids encoding antibodies including one or more CDRs shown in Table 1, nucleic acids encoding antibodies that have the polypeptide sequence of the antibodies produced by a HIC0 4-F9, HIC1 2-B4, HIC1 4-G6, HIC1 7-H10, HIC0 3-C5, HIC1 5-F10, DHIC2 2-B4, or DHIC2 2-C12 hyridoma; DHIC2 4-A10 or DHIC3 5-H10 hybridoma; or a HIC1 1-C10 hybridoma (or a humanized form of any of these antibodies) can readily be produced by one of skill in the art.

Exemplary nucleic acid sequences are as follows:

TABLE 3

| Hybridoma ID | Nucleotide sequence for heavy chain V-region |
|---|---|
| HIC0-4F9 | CAGAAGTTCAGCTGCAGCAGTCTGGGGCTGAGCTTGTG AGGCCAGGGGCCTTAGTCAAGTTGTCCTGCAAAGCTTC TGGCTTCAATATTAAAGACTACTATATACACTGGGTGA AGCAGAAGCCTGAACAGGGCCTGGAGTGGATTGGATGG ATTGATCCTGAGAATGGTAATACTATATATGACCCGAA GTTCCAGGACAAGGCCAGTATAACTTCAGACACATCCT CCAACACAGCCTACCTCCAGCTCAGCAGCCTGACATCT GAGGCACTGCCGTCTATTACTGTACTAGTTACTACGG TAGTACCTACTACTTTGACTACTGGGGCCAAGGCACCA (SEQ ID NO: 29) |
| DHIC2 2-C12 | ATGGCGGCGGCGCAGAGCATTCAGGTGCAGATTCAGCT GGTGCAGAGCGGCCCGGAACTGAAAAAACCGGGCGAAA CCGTGAAAATTAGCTGCAAAGCGAGCGGCTATACCTTT ACCGATTATAGCATGCATTGGGTGAAACAGGCGCCGGG CAAAGGCCTGAAATGGATGGGCTGGATTAACACCGAAA CCGGCGAACCGACCTATGCGGATGATTTTAAAGGCCGC TTTGCGTTTAGCCTGGAAACCAGCGCGAGCACCGCGTA TCTGCAGATTAACAACCTGAAAAACGAAGATACCGCGA CCTATTTTGCAGCCGCGGCTATGGCAGCAGCAGCTGG TTTGCGTATTGGGGCCAGGGCACCCTGGTGACCGTGAG CGCGGAAAGCCAGAGCTTTCCGAAC (SEQ ID NO: 30) |
| HIC0 3-C5 | TGAAGTGATGCTGGTGGAGTCTGGGGGAGGCTTAGTGA AGCCTGGAGGGTCCCTGAAACTCTCCTGTGCAGCCTCT GGATTCACTTTCAGTAACTATGCCATGTCTTGGGTTCG CCAGACTCCGGAGAAGAGGCTGGAGTGGGTCGCAACCA TTAGTAGTGGTGGTAGTTACACCTACTATCCAGACAGT GTGAAGGGGCGATTCACCATCTCCAGAGACAATGCCAA GAACACCCTGTACCTGCAAATGAGCAGTCTGAGGTCTG |

TABLE 3-continued

| Hybridoma ID | Nucleotide sequence for heavy chain V-region |
|---|---|
| | AGGACACGGCCATGTATTACTGTGCAAGACAGGGGGAT AACTACTGGTACTTCGATGTCTGGGGCGCAGGGACCAC GGTCACCGTCTCCTCAGAGAGTCAGTC (SEQ ID NO: 31) |
| HIC1 5-F10 | GAGTGGTGCCTTGGCCCCAATAATCAAAATACTTCTCG TGTCTTGCACAGAAATAGACCGCAGAGTCTTCAGATGT CAATCTACTAAGTTCCATATAGACTGTGCTGGAGGATT TGTCCGCAGTCAATGTGGCCTTGTCCTTGAATTTCTCA CTGTACTTTAGACCACCACTTCCAGGGTAAAACCACCC AATCCACTCAAGACCCTGTCCAGACCTCTGCTTTACCC AGTGTATAATATACTCAGTGAAGGTGTAGCCAGAAGCC TTGCAGGACAGCTTCACTGATGCCCCGGGTTTCACCAG CTCAGCTCCAGACTGCTGCAGCTGGAC (SEQ ID NO: 32) |
| HIC1 4-G6 | TGAGGTGAAGCTGGTGGAGTCTGGAGGAGGCTTGGTAC AGCCTGGGGGTTCTCTGAGACTCTCCTGTGCAACTTCT GGATTCACCTTCACTGATTACTACATGCACTGGGTCCG CCAGCCTCCAGGAAAGGCACTTGAGTGGTTGGGTTTTA TTAGAAACAAAGCTAATGGTTACACAACAGAGTACAGT GCATCTGTGAAGGGTCGGTTCACCATCTCCAGAGATAA TTCCCAAAGCATCCTCTATCTTCAAATGAACACCCTGA GAGCTGAGGACAGTGCCACTTATTACTGTACAAGAGAT ATAAAGGGGGACTACTGGGGTCAAGGAACCTCAGT (SEQ ID NO: 33) |
| HIC1 7-H10 | GAGTCCCTTGGCCCCAATAAGCAAACCAGGGTTGGTTA CCCCCATGTCTTGTACAGTAATACATGGCTGTGTCTTC AGACCTCAGACTGCTCATCTGCAGGGACAGGGTGTTCT TGGCATTGTCTCTGGAAATGGTGAATCGGCCCTTCACA GTGTTTGGAAAGTAGGTGCTACCACCACCACTACTAAT GTATGCGACCCACTCCAGCCTCTTGTCCGGAGCCTGGC GAACCCAAGACATGTCATAGCTACTGAAAGCGAATCCA GAGGCTGCACAGGAGAGTTTCAGGGACCCTCCAGGCTT CACTAAGCCTCCCCCAGACTCCACCAGTTGCACTTCA (SEQ ID NO: 34) |

Nucleotides molecules encoding the antibodies can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same effector molecule ("EM") or antibody sequence. Thus, nucleic acids encoding antibodies, conjugates and fusion proteins are provided herein.

Nucleic acid sequences encoding the antibodies that specifically bind pancreatic endocrine cells or a subset thereof, nucleic acid sequences encoding the antibodies that specifically bind pancreatic exocrine cells, and nucleic acid sequences encoding the antibodies that specifically bind pancreatic ductal cells can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding sequences encoding an antibody that specifically binds pancreatic endocrine cells or a subset thereof, an antibody that specifically binds pancreatic exocrine cells or a subset thereof, or an antibody that specifically binds pancreatic ductal cells or a subset thereof can be prepared by cloning techniques. Examples of appropriate cloning and sequencing techniques, and instructions sufficient to direct persons of skill through cloning are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill In one example, an antibody of use is prepared by inserting the cDNA which encodes a variable region from an antibody into a vector which comprises the cDNA encoding an effector molecule (EM), such as an enzyme or label. The insertion is made so that the variable region and the EM are read in frame so that one continuous polypeptide is produced. Thus, the encoded polypeptide contains a functional Fv region and a functional EM region. In one embodiment, cDNA encoding an enzyme is ligated to a scFv so that the enzyme is located at the carboxyl terminus of the scFv. In several examples, cDNA encoding a horseradish peroxidase or alkaline phosphatase, or a polypeptide marker of interest is ligated to a scFv so that the enzyme (or polypeptide marker) is located at the amino terminus of the scFv. In another example, the label is located at the amino terminus of the scFv. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds. In a yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the immunotoxin, antibody, labeled antibody, or fragment thereof are isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding the antibody, labeled antibody, or functional fragment thereof, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, labeled antibody, or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the antibody, labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labeled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis, Part A.* pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

Methods of Detection and Isolation

A method is provided herein for the detection and/or isolation of pancreatic endocrine cells or a subset thereof from a biological sample or cells in vitro. These methods include contacting cells with one or more of the antibodies disclosed herein that specifically bind a cell surface antigen on pancreatic endocrine cells to form an immune complex. The presence (or absence) of the immune complex is then detected and/or used to isolate cells of interest. Pancreatic endocrine cells can be detected either in vivo or in vitro. Thus, in one example, the methods disclosed herein can be used to detect the number or mass of pancreatic endocrine cells (or a subset thereof) in a subject, such as a human subject.

In one embodiment a reduction in the number or mass of pancreatic endocrine cells, as compared to a control, indicates that the subject has or is at risk of having diabetes. The number and or mass of all types of pancreatic endocrine cells, or a specific subset, such as the insulin producing cells, can be determined using the methods disclosed herein. A control can be a standard value, or the number or mass of pancreatic endocrine cells in a sample from a subject not afflicted with diabetes, or the number or mass of pancreatic endocrine cells in a subject not afflicted with diabetes. In another embodiment, an increase in the number or mass of pancreatic endocrine cells, as compared to a control, indicates that the subject has a pancreatic endocrine cell tumor. Thus, an increase in the number of pancreatic endocrine cells, or the pancreatic endocrine cell mass, as compared to a subject without a pancreatic endocrine cell tumor, indicates that the subject has, or is at risk of having, a pancreatic endocrine cell tumor. In a further embodiment, the method is used to indicate if a therapeutic treatment is effective in a subject. Thus, in one example, the therapy is designed to increase or maintain the number (or mass) of pancreatic endocrine cells, as compared to a subject without treatment. Maintenance of pancreatic endocrine cell tissue, or an increase in the number of pancreatic endocrine cells, as compared to a control, indicates that the treatment is effective. In another example, the therapy is designed to decrease the number (or mass) of pancreatic endocrine cells, such as for tumor treatment. A decrease in the number of pancreatic endocrine cells in the tumor, or a decrease in tumor mass, indicates that the treatment is effective.

Methods are also provided herein for the detection of pancreatic exocrine cells. A method is provided herein for the detection and/or isolation of pancreatic exocrine cells or a subset thereof from a biological sample or cells in vitro. These methods include contacting cells with one or more of the antibodies disclosed herein to form an immune complex. The presence (or absence) of the immune complex is then detected and/or used to isolate cells of interest. Pancreatic exocrine cells can be detected either in vivo or in vitro. Thus, in one example, the methods disclosed herein can be used to detect the number or mass of pancreatic exocrine cells (or a subset thereof) in a subject, such as a human subject.

In one example, the methods are used to detect a pancreatic exocrine cell tumor. The number and or mass of pancreatic exocrine cells can be determined using the methods disclosed herein. In one embodiment, an increase in the number or mass of pancreatic exocrine cells, as compared to a control, indicates that the subject has a pancreatic exocrine cell tumor. A control can be a standard value, or the number or mass of pancreatic exocrine cells in a sample from a subject not afflicted with a tumor. Thus, an increase in the number of pancreatic exocrine cells, or the pancreatic exocrine cell mass, as compared to a subject without a pancreatic exocrine cell tumor, indicates that the subject has, or is at risk of having, a pancreatic exocrine cell tumor.

A method is also provided herein for detecting pancreatic ductal cells. In one example, methods are provided for detecting a pancreatic adenocarcinoma. A method is provided herein for the detection and/or isolation of pancreatic ductal cells or a subset thereof from a biological sample or cells in vitro. These methods include contacting cells with the antibodies disclosed herein that specifically bind pancreatic ductal cells to form an immune complex. The presence (or absence) of the immune complex is then detected and/or used to isolate cells of interest. Pancreatic ductal cells can be detected either in vivo or in vitro. Thus, in one example, the methods disclosed herein can be used to detect the number or mass of pancreatic ductal cells (or a subset thereof) in a subject, such as a human subject.

In one example, the methods are used to detect a pancreatic adenocarcinoma. The number and or mass of pancreatic ductal cells can be determined using the methods disclosed herein. In one embodiment, an increase in the number or mass of pancreatic ductal cells, as compared to a control, indicates that the subject has a pancreatic adenocarcinoma. A control can be a standard value, or the number or mass of pancreatic ductal cells in a sample from a subject not afflicted with an adenocarcinoma. Thus, an increase in the number of pancreatic ductal cells, or the pancreatic ductal cell mass, as compared to a subject without a pancreatic adenocarinoma, indicates that the subject has, or is at risk of having, a pancreatic adenocarcinoma.

In one embodiment, a sample is obtained from a subject, and the presence of pancreatic endocrine cells, or pancreatic endocrine cell subset, is assessed in vitro. In another embodiment, a sample is obtained from a subject, and the presence of pancreatic exocrine cells, or pancreatic exocrine cell subset, is assessed in vitro. In a further embodiment, a sample is obtained from a subject, and the presence of pancreatic ductal cells is assessed in vitro. A biological sample for in vitro testing is typically obtained from a mammalian subject of interest, such as a rat, mouse, cow, dog, guinea pig, rabbit, or primate, such as a non-human or a human primate. In one embodiment, the primate is macaque, chimpanzee, or a human.

In a further embodiment, when assessing pancreatic endocrine cells, the subject has, is suspected of having, or is at risk of developing diabetes. In another embodiment, when assessing pancreatic endocrine cells, the subject has, is suspected of having, or is at risk of having a tumor of the pancreatic endocrine cells, such as an insulinoma. In yet another embodiment, when assessing pancreatic exocrine cells, the subject has, is suspected of having, or is at risk of having, a pancreatic exocrine cell tumor. In an additional embodiment, when assessing pancreatic ductal cells, the subject has, is suspected of having, or is at risk of having a pancreatic adenocarcinoma.

The sample can be any sample, including, but not limited to, tissue from biopsies, autopsies and pathology specimens. Biological samples also include sections of tissues, for example, frozen sections taken for histological purposes. If desired, the antigen of interest can also be detected in additional biological samples. Biological samples further include body fluids, such as blood, serum, spinal fluid, pancreatic ductal fluid or urine.

The antibodies described herein can be used in immunohistochemical assays. These assays are well known to one of skill in the art (see Harlow & Lane, *Antibodies, A Laboratory Manual*, Cold Spring Harbor Publications, New York (1988), for a description of immunoassay formats). The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). The antibodies can also be used for magnetic separation of endocrine cells, exocrine cells and/or ductal cells. Magnetic separation involves the use of paramagnetic particles which are: 1) conjugated to the pancreatic specific antibodies, such as endocrine cell specific antibodies, exocrine cell antibodies and/or ductal cell antibodies; 2) conjugated to detection antibodies which are able to bind to the pancreatic specific antibodies; or 3) conjugated to a detection reagent (such as avidin) which can bind to detection antibodies (such as biotinylated antibodies). Any of the antibodies disclosed herein can be used in these assays. The antibodies can be used in methods that utilize positive selectin (expressing the antigen of interest), negative selection (not expressing the antigen of interest), or both (expressing one antigen of interest and not expressing a second antigen of interest).

An application of the antibodies described herein is the assessment of purity and/or functionality of a clinically-relevant pancreatic population, such as an islet cell preparation, obtained from a cadaveric donor. Prior to transplantation to a human recipient, the extent of labeling of intact islets or dissociated islet cells by these antibodies can provide a useful measure of their quality and suitability for transplantation. This extent of labeling could be determined by flow cytometry, immunocytochemistry, or by protein recognition in an ELISA assay.

In some embodiments, methods are provided for isolating pancreatic endocrine cells, a specific type of pancreatic endocrine cells, cells exhibiting glucose-dependent insulin secretion, or islets of Langerhans, using the antibodies disclosed herein. Protocols for the isolation of islets are well known in the art, see for example, Kinasiewicz et al., *Physiol. Res.* 53: 327-333, 2004. These protocols can include both positive selection (for pancreatic endocrine cells) and negative selection (so that exocrine cells and/or ductal cells are excluded). Thus, in several examples, the antibodies disclosed herein can be used in the isolation of pancreatic endocrine cells, or a subset thereof, from the pancreas. However, pancreatic endocrine cells also can be isolated from culture systems designed to produce pancreatic endocrine cells. For example, the production of endocrine cells from ES cells is described in PCT Application No. PCT/US02/02361. Pancreatic endocrine cells can also be isolated from proliferating cells of human cadaveric islets or other pancreatic tissue in vitro. In one embodiment, the epithelial cells migrate out from the islets of Langerhans when cultured ex vivo and undergo an epithelial to mesenchymal transition to form a population of mesenchymal cells (see Gershengorn et al., Science 306(5705):2261-4. Epub Nov. 25, 2004). These committed mesenchymal cells can then undergo a mesenchymal to epithelial transition to form endocrine cells. In another embodiment, non-islet exocrine cells may be cultured and induced to adopt an endocrine phenotype (see Todorov et al., Pancreas 32(2):130-138, 2006). Both the non-islet exocrine cells and the cells that are induced to adopt an endocrine phenotype can be identified using the antibodies disclosed herein.

In one example, cultures can be initiated by labeling of live cells with duct-specific antibodies and isolation of positive cells using FACS or immunomagnetic separation. Alternatively, depletion of cells expressing endocrine-specific antigens (and/or exocrine-specific antigens) could be employed to enrich for exocrine and duct cells. An endocrine phenotype can then be induced, and labeling with endocrine-specific antibodies then permits the non-destructive isolation of the subpopulation of cells that had begun to express and endocrine hormone, such as insulin.

Pancreatic endocrine cells (or a subset thereof) can further be generated from liver cells (see Kojima et al., Nat. Med. (5):596-603. Epub 2003 Apr. 21, 2003). Pancreatic endocrine cells produced by these methods, or any other method known to one of skill in the art, can be isolated from other cell types using the antibodies disclosed herein.

In several examples, the isolated pancreatic endocrine cells or a subset thereof are cultured in vitro, used in drug screening assays (such as to identify agents of use in treating diabetes or pancreatic endocrine cell tumors), or can be transplanted into a subject. Similarly, isolated pancreatic exocrine cells or ductal cells can be cultured in vitro, and used in drug screening assays (such as to identify agents of use in treating pancreatic exocrine cell tumors or pancreatic adenocarcinomas, respectively). The methods include contacting the isolated pancreatic cells with an agent of interest and detecting the effect of the agent of interest on the pancreatic cells as compared to a control (such as a cell contacted with a vehicle, or a cell not contacted with the agent). In several examples, the ability of the agent to cause death of the pancreatic cells, or to decrease cell division, is assessed. An increase in cell death, or a decrease in cell division, indicates the agent is of use to treat pancreatic cancer. In another example, the ability of the agent to alter secretion by the pancreatic cells is assessed.

In one embodiment, suspension of cells including pancreatic endocrine cells is produced, and one or more of the antibodies disclosed herein is/are reacted with the cells in suspension. Methods of determining the presence or absence of a cell surface marker are well known in the art. Typically, labeled antibodies specifically directed to the marker are used to identify the cell population.

Antibodies can be conjugated to other compounds including, but not limited to, enzymes, paramagnetic beads, colloidal paramagnetic beads, haptens, fluorochromes, metal compounds, radioactive compounds or drugs. The enzymes that can be conjugated to the antibodies include, but are not limited to, alkaline phosphatase, peroxidase, urease and β-galactosidase. The fluorochromes that can be conjugated to the antibodies include, but are not limited to, fluorescein isothiocyanate, tetramethylrhodamine isothiocyanate, phycoerythrin, allophycocyanins and Texas Red. For additional fluorochromes that can be conjugated to antibodies see Haugland, R. P., *Molecular Probes: Handbook of Fluorescent Probes and Research Chemicals* (1992-1994). The metal compounds that can be conjugated to the antibodies include, but are not limited to, ferritin, colloidal gold, and particularly, colloidal superparamagnetic beads. The haptens that can be conjugated to the antibodies include, but are not limited to, biotin, digoxigenin, oxazalone, and nitrophenol. The radioactive compounds that can be conjugated or incorporated into the antibodies are known to the art, and include but are not limited to technetium 99m ($^{99}$Tc), $^{125}$I and amino acids comprising any radionuclides, including, but not limited to, $^{14}$C, $^{3}$H and $^{35}$S. Additional reagents are described above, and/or are known in the art.

Fluorescence activated cell sorting (FACS) can be used to detect and/or separate pancreatic endocrine cells (or a subset thereof) by contacting the cells with an appropriately labeled antibody. FACS can also be used to detect and/or separate pancreatic exocrine cells and/or pancreatic ductal cells. In one embodiment, additional antibodies and FACS sorting can further be used to produce isolated populations of pancreatic cells, such as but not limited to pancreatic endocrine cells. Combinations of the antibodies disclosed herein can be utilized in order to maximize the selectivity. An example would be the isolation of HIC1 2-B4$^{positive}$ DHIC2 2-C12$^{negative}$ HIC1 1-C10$^{negative}$ DHIC3 5-H10$^{negative}$ cells, which are positive for an endocrine marker and negative for markers of alpha cell, exocrine cell, and duct cell identity. FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells (for exemplary methods of FACS see U.S. Pat. No. 5,061,620, herein incorporated by reference).

However, other techniques of differing efficacy may be employed to isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required. Separation procedures may include magnetic separation, using antibody-coated paramagnetic beads, affinity chromatography, cytotoxic agents, either joined to a monoclonal antibody or used in conjunction with complement, and "panning", which utilizes a monoclonal antibody attached to a solid matrix, or another convenient technique. Antibodies attached to paramagnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (such as an antigen that binds one or more of the monoclonal antibodies disclosed herein) to bind to the solid-phase linked antibodies. The bound cells are then separated from the solid phase by any appropriate method, depending mainly upon the nature of the solid phase and the antibody employed.

In one specific, non-limiting example, pancreatic endocrine cells or a subset thereof are positively selected by paramagnetic bead separation, wherein paramagnetic beads are coated with a monoclonal antibody that specifically binds pancreatic endocrine cells as disclosed herein. The cells that are specifically bound by the monoclonal antibody are then removed from the paramagnetic beads. Release of the cells from the paramagnetic beads can be effected by methods known in the art. The purity of the isolated cells is then checked with a FACSCAN® flow cytometer (Becton Dickinson, San Jose, Calif.), for example, if so desired. In one embodiment, paramagnetic bead separation is used to first separate a population of cells that do not express a marker, such as pancreatic exocrine cell markers (for panning methods see Small et al., *J Immunol Methods* 3; 167(1-2):103-7, 1994, herein incorporated by reference.

Similar methods can be used to isolate pancreatic exocrine cells or pancreatic ductal cells, using paramagnetic beads coated with an antibody that specifically bind pancreatic exocrine cells or pancreatic ductal cells, respectively. In some embodiments of these methods, paramagnetic bead separation is first used to separate cells that do not express pancreatic endocrine cell markers.

The antibodies disclosed herein can also be used to distinguish between useful and contaminating cells in cultures intended to produce endocrine cells or a subset thereof, such as beta cells (or pancreatic ductal cells). A variety of different cell sources and/or culture environments can be used to produce beta cells in vitro (see above); the antibodies disclosed herein can be used to select cells of interest.

The antibodies disclosed herein can also be used to assess the efficacy of culture conditions. For example, the effectiveness of adding amount of a growth factor, nutrient or cytokine to an in vitro culture conditions can be evaluated. In one example, an efficient yield of endocrine cells indicates that the culture method can be used to efficiently produce endocrine cells or a subset thereof. For example, endocrine cells can be generated using a standard set of culture conditions and a test set of culture conditions. The number of endocrine cells generated under the two sets of conditions can then be assessed. In one example, an increase in the number of endocrine cells generated using the test conditions indicate that these conditions are effective from the production of pancreatic endocrine cells.

In one example, the antibodies disclosed herein are used to isolate and/or identify cells capable of initiating, maintaining, or enhancing epithelial-to-mesenchymal-transition (EMT) cultures. These cultures are established using human islet cell preparations, generally preparations of cadaveric islets, and yield large numbers of cells with a detectable level of glucose-responsive insulin secretion (see Gershengorn et al., supra, 2004). Cells capable of initiating, maintaining, or enhancing non-islet derived cell cultures that yield insulin-secreting progeny can be isolated and/or identified (see Todorov et al., Pancreas 32(2):130-138, 2006). In another example, the antibodies disclosed herein are used to identify and/or select cells differentiated from embryonic stem cells. Thus, the pre-culture input or post-culture output of cells in such cultures can be optimized by viable selection using the antibodies disclosed herein.

The antibodies disclosed herein can also be used to detect pancreatic endocrine cells or a subset thereof, pancreatic exocrine cells, or pancreatic ductal cells in vivo. The antibodies disclosed herein can also be used to detect pancreatic tumors in vivo. In one embodiment, a monoclonal antibody that binds the pancreatic cell population of interest is administered to the subject for a sufficient amount of time for the antibody to localize to the pancreas (or tumor) in the subject and to form an immune complex with the pancreatic cells (or tumor). The immune complex can then be detected. In one specific, non-limiting example detection of an immune complex is performed by immunoscintography. Other specific, non-limiting examples of immune complex detection include radiolocalization, radioimaging, magnetic resonance imaging or fluorescence imaging. Once detected, in an ectopic location (as in a tumor) the test results can be used to assist in or guide surgical or other excision of a tumor. In one embodiment, the antibody is linked to an effector molecule. In one specific, non-limiting embodiment, the effector molecule is a detectable label. Specific, non-limiting examples of detectable labels include a radioactive isotope, an enzyme substrate, a co-factor, a ligand, a chemiluminescent agent, a fluorescent agent, an electron dense reagent, a hapten, or an enzyme. In several examples, the antibody specifically binds pancreatic endocrine cells, pancreatic exocrine cells, or pancreatic ductal cells.

The antibodies disclosed herein can be used to target a therapeutic agent to pancreatic cells. Treating pancreatic cells (as in a tumor) in a subject includes the administration of a monoclonal antibody complexed to an effector molecule, such as, but not limited to, a radioactive isotope or other chemotherapeutic agent. In one embodiment, the antibody is complexed to an effector molecule, such as a radioactive isotope, is administered to a subject prior to surgery or treatment. In one example, an antibody that specifically binds pancreatic endocrine cells is administered to a subject prior to treatment for diabetes or an endocrine cell tumor. In another embodiment, the antibody complexed to an effector molecule, such as a radioactive isotope, is administered to a subject following surgery or treatment. Thus, in another example, an antibody that specifically binds pancreatic endocrine cells is administered to a subject following treatment for diabetes or a tumor. After a sufficient amount of time has elapsed to allow for the administered radiolabeled antibody to localize to cells of interest, the islet cells or tumor is detected. In additional examples, an antibody that specifically binds ductal cells can be administered to a subject prior to, or following, treatment for a pancreatic adenocarcinoma. Thus, the effectiveness of the treatment can be assessed.

In one embodiment, an antibody that specifically binds a cell surface antigen on pancreatic cells and a secondary antibody are administered to the subject for a sufficient amount of time for the monoclonal antibody to form an immune complex on a pancreatic cell, (such as, but not limited to, in the pancreatic islets of Langerhans and/or a tumor) and for the secondary antibody to form an immune complex with the monoclonal antibody that binds pancreatic cells (such as, but not limited to, in the pancreatic islets of Langerhans and/or a tumor). In one embodiment, the antibody that binds pancreatic cells is complexed with the secondary antibody prior to their administration to the subject. In one specific, non-limiting embodiment, the secondary antibody is linked to a detectable label. In one embodiment, the immune complex, which includes a pancreatic cell, the monoclonal antibody that binds the pancreatic cell, and the secondary antibody linked to a detectable label, is detected as described above. In several examples, the pancreatic cell is a pancreatic endocrine cell, a pancreatic exocrine cell, or a pancreatic ductal cell.

Thus, in vivo imaging methods can also be utilized with the antibodies disclosed herein. These technologies include magnetic resonance imaging, positron emission tomography, and optical imaging. Advances in beta cell imaging using these technologies were recently reviewed (see Paty et al., Transplantation. 77:1133-1137, 2004, herein incorporated by reference). The methods include magnetic resonance imaging (such as using an biotinylated antibody and avidin-iron oxide), positron emission tomography (such as using an $^{111}$indium-labeled monoclonal antibody), and optical imaging (such as using luciferase or green fluorescent protein labeled antibodies). Recent data from the mouse indicates that beta cells in the pancreas can be imaged using intact monoclonal antibodies, although the use of antibody fragments is also contemplated.

In one example, magnetic resonance imaging is utilized. In the setting of magnetic resonance imaging, contrast agent detection can be greatly impacted by magnetic resonance scanner field strength. Increased field strengths provide improvements by orders of magnitude in the ability to detect contrast agents (Hu et al., Annu Rev Biomed Eng. 6:157-184, 2004; Wedeking et al., Magn. Reson. Imaging. 17:569-575, 1999). For example, the limit of detection of gadolinium at 2 tesla (T) is ~30 µM. At 4T the limit of detection is reduced to ~1 µM. With newly available 7 to 12T scanners one would expect to detect low (10-100) nM concentrations of this contrast agent. Similar sensitivity can also be identified using contrast agents such as iron oxide.

Kits are also provided herein. Kits for detecting pancreatic endocrine cells or a subset thereof will typically comprise an antibody that specifically binds a cell surface antigen on pancreatic endocrine cells, such as any of the antibodies described herein. Kits for detecting pancreatic exocrine cells will typically comprise an antibody that specifically binds a cell surface antigen on pancreatic exocrine cells, such as any of the antibodies described herein. Kits for detecting pancreatic ductal cells will typically comprise an antibody that specifically binds a cell surface antigen on pancreatic ductal cells, such as any of the antibodies described herein. More than one of the antibodies disclosed herein can be included in the kit. Thus, the kit can include two or more of an antibody that specifically binds pancreatic endocrine cells, and/or an antibody that specifically binds pancreatic exocrine cells, and/or an antibody that specifically binds pancreatic ductal cells. In some embodiments, an antibody fragment, such as an Fv fragment is included in the kit. In one example, such as for in vivo uses, the antibody can be a scFv fragment. In a further embodiment, the antibody is labeled (for example, with a fluorescent, radioactive, or an enzymatic label).

In one embodiment, a kit includes instructional materials disclosing means of use of an antibody that specifically binds pancreatic cells. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting pancreatic cells (such as pancreatic endocrine cells or a subset thereof) in a biological sample generally includes the steps of contacting the biological sample with an antibody which specifically reacts, under immunologically reactive conditions, to the pancreatic cells of interest (such as endocrine cells). The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, paramagnetic beads, colloidal magnetic beads, haptens, fluorochromes, metal compounds, radioactive compounds or drugs, as described herein. The antibodies can also be utilized in immunoassays such as but not limited to radioimmunoassays (RIAs), enzyme linked immunosorbant assays (ELISA), or immunohistochemical assays.

Pharmaceutical Compositions and Therapeutic Methods

Pharmaceutical compositions are disclosed herein that include an antibody that specifically binds pancreatic cells, such as pancreatic endocrine cells or a subset thereof, pancreatic exocrine cells, or pancreatic ductal cells (including a humanized form thereof or a functional fragments thereof). These pharmaceutical compositions are for use in methods of treatment and/or methods of detection, and can be formulated with an appropriate solid or liquid carrier, depending upon the particular mode of administration chosen. In addition, a monoclonal antibody linked to an effector molecule (i.e., toxin, chemotherapeutic drug, or detectable label) can be prepared in pharmaceutical compositions. Compositions including an antibody that specifically binds pancreatic endocrine cells or a subset thereof are of use, for example, for the treatment of pancreatic endocrine cell tumors, such as, but not limited to, insulinomas, glucagonomas, or multiple endocrine neoplasm type 1 (MEN-1). Compositions including an antibody that specifically binds pancreatic exocrine cells are of use, for example, for the treatment of pancreatic exocrine cell tumors. Compositions including an antibody that specifically binds pancreatic ductal cells are of use, for example, for the treatment of pancreatic adenocarcinoma.

The pharmaceutically acceptable carriers and excipients useful in this disclosure, for either therapeutic or diagnostic methods, are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, other proteins, such as human serum albumin or plasma preparations. If desired, the pharmaceutical composition to be administered can also contain minor amounts of non-toxic auxiliary substances, such as wetting or emulsifying agents, preservatives, and pH buffering agents and the like, for example sodium acetate or sorbitan monolaurate.

The dosage form of the pharmaceutical composition will be determined by the mode of administration chosen. For instance, in addition to injectable fluids, topical, inhalation, oral and suppository formulations can be employed. Topical preparations can include ointments, sprays and the like. Inhalation preparations can be liquid (such as solutions or suspensions) and include mists, sprays and the like. Oral formulations can be liquid (for example, syrups, solutions or suspensions), or solid (such as powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

The pharmaceutical compositions that include a monoclonal antibody can be formulated in unit dosage form suitable for individual administration of precise dosages. In addition, the pharmaceutical compositions may be administered in a single dose or as in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner. In one specific, non-limiting example, a unit dosage can be about 0.1 to about 10 mg per patient per day. Dosages from about 0.1 up to about 100 mg per patient per day may be used, particularly if the agent is administered to a secluded site and not into the circulatory or lymph system, such as into a body cavity, into a lumen of an organ, or directly into a tumor. In one embodiment, about 10 mCi of a radiolabeled monoclonal antibody is administered to a subject. In other embodiments, about 15 mCi, about 20 mCi, about 50 mCi, about 75 mCi or about 100 mCi of a radiolabeled monoclonal antibody is administered to a subject. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The compounds of this disclosure can be administered to humans on whose tissues they are effective in various manners such as administration into the tumor. However, administration topically, orally, intravascularly such as intravenously, intramuscularly, intraperitoneally, intranasally, intradermally, intrathecally, subcutaneously, via inhalation or via suppository is of use with the antibodies disclosed herein. The particular mode of administration and the dosage regimen will be selected by the attending clinician, taking into account the particulars of the case (for example the subject, the disease, the disease state involved, and whether the treatment is prophylactic).

In one embodiment, a therapeutically effective amount of an antibody is the amount necessary to inhibit further growth of pancreatic endocrine cell tumor, a pancreatic exocrine cell tumor, or a pancreatic adenocarcinoma, or the amount that is effective at reducing a sign or a symptom of the tumor. In another embodiment, a therapeutically effective amount of an antibody is the amount sufficient to visualize pancreatic cells in a subject, such as but not limited to pancreatic endocrine cells (or a subset thereof) in the islets of Langerhans of the pancreas. It is advantageous for this dose to be administered in a human subject without eliciting a human anti-mouse (HAMA) response in the subject receiving the treatment.

Controlled release parenteral formulations of a monoclonal antibody can be made as implants, oily injections, or as particulate systems. For a broad overview of protein delivery systems (see Banga, A. J., Therapeutic Peptides and Proteins: Formulation, Processing, and Delivery Systems, Technomic Publishing Company, Inc., Lancaster, Pa., 1995). Particulate systems include microspheres, microparticles, microcapsules, nanocapsules, nanospheres, and nanoparticles. Microcapsules contain the therapeutic protein as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, J., Colloidal Drug Delivery Systems, J. Kreuter, ed., Marcel Dekker, Inc., New York, N.Y., pp. 219-342, 1994; Tice & Tabibi, Treatise on Controlled Drug Delivery, A. Kydonieus, ed., Marcel Dekker, Inc. New York, N.Y., pp. 315-339, 1992).

Polymers can be used for ion-controlled release. Various degradable and nondegradable polymeric matrices for use in controlled drug delivery are known in the art (Langer, R., *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec et al., *J. Parent. Sci. Tech.* 44:58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri, et al., Liposome Drug Delivery Systems, Technomic Publishing Co., Inc., Lancaster, Pa., 1993). Numerous additional systems for controlled delivery of therapeutic proteins are known (see, for example, U.S. Pat. Nos. 5,055,303, 5,188,837, 4,235,871, 4,501,728, 4,837,028 4,957,735 and 5,019,369, 5,055,303; 5,514,670; 5,413,797; 5,268,164; 5,004,697; 4,902,505; 5,506,206, 5,271,961; 5,254,342 and 5,534,496).

Site-specific administration of the disclosed compounds can be used, for instance by applying the antibody a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody may be beneficial.

The present disclosure also includes therapeutic uses of monoclonal antibodies that are non-covalently or covalently linked to effector molecules. In one specific embodiment, the monoclonal antibody is covalently linked to an effector molecule that is toxic to a pancreatic tumor. In one specific, non-limiting example, the effector molecule is a cytotoxin. In other specific, non-limiting examples the effector molecule is a radioactive isotope, a chemotherapeutic drug, a bacterially-expressed toxin, a virally-expressed toxin, a venom protein, or a cytokine. Monoclonal antibodies covalently linked to an effector molecule have a variety of uses. For example, an antibody linked to a radioactive isotope is of use in immunotherapy. An antibody covalently linked to a radioactive isotope is of use to localize a tumor in radioimmunoguided surgery, such that the tumor can be removed.

The present disclosure also includes combinations of a monoclonal antibody, with one or more other agents useful in the treatment of tumors. For example, the compounds of this disclosure can be administered in combination with effective doses of immunostimulants, anti-cancer agents (such as chemotherapeutics), and/or vaccines. The term "administration in combination" or "co-administration" refers to both concurrent and sequential administration of the active agents.

The disclosure is illustrated by the following non-limiting Examples.

EXAMPLES

Example 1

Monoclonal Antibodies

For the generation of these antibodies, BALB/c mice were immunized with whole cells (either intact islets or enzyme-dispersed islet cells), and two different immunization strategies have been used. The two immunization strategies include a "standard method" where animals are immunized with desired target cells or a "subtractive method" designed to limit reactivity against undesirable antigens (Brooks et al., J. Cell Biol. 122:1351-1359, 1993; Sleister et al., J Immunol Methods 252:121-129, 2001; Sleister et al., J Immunol Methods. 261:213-220; Zijlstra et al., Biochem Biophys Res Commun. 303:733-744, 2003). For subtractive immunizations, mice were first given 2 million human peripheral blood leukocytes (PBL) (as a source of undesirable human antigens), followed by administration of cyclophosphamide on days 1 and 2 after this initial immunization to ablate B-cells reactive with the undesirable PBL-associated antigens. The "subtracted" mice were then immunized 2 times with preparations of enriched islet cells obtained as islet equivalents from the Islet Cell Resource Centers. For standard immunizations, mice were immunized 2-3 times with enriched islet cells. Four days after the final boosts (for both immunization strategies), splenocyes were fused with SP2/0 myeloma cells and plated in methylcellulose media. 600-800 hybridoma clones (from each fusion) were picked after 10-14 days of growth, and subcultured in 96-well plates. Supernatant from each clone was then used to stain acetone fixed frozen human pancreas sections in a primary screen, with a fluorochrome-conjugated polyclonal anti-mouse immunoglobulin used to detect section-bound unlabeled primary antibodies. Stained sections were analyzed by fluorescence microscopy for novel antibodies reacting with discrete pancreatic cell subsets.

These fusions have yielded a large panel of antibodies that react with different pancreatic cell subsets (Table 3). Monoclonal antibodies were developed against pancreatic endocrine cells. The cell specificity of each monoclonal antibody was determined by real time polymerase chain reaction using FACS sorted cells. For the determination, cells were sorted using the specified monoclonal antibody, and the sorted cells were evaluated for mRNA encoding insulin ($\beta$ cells) or glucagon ($\alpha$ cells). Ratios of close to one indicate that message for both molecules was present, a ratios of much higher than one indicates selective expression of insulin, and ratios of much less than one indicate selective expression of glucagon. Alternatively, cell specificity was determined by two-color immunohistochemistry. Digital images obtained from immunohistochemical studies using monoclonal antibodies that define cellular targets in pancreatic islets, are illustrated in FIG. 1. Each panel in this figure illustrates staining with antibody from an independently derived hybridoma. Panels HIC0 4-F9, HIC1 2-B4, HIC1 4-G6, HIC1 5-F10 and HIC1 7-H10 illustrate staining of all islet cells (pan-islet). The panel labeled HIC0 3-C5 illustrates staining with an antibody that binds to a subset of endocrine cells (including a subset of ($\beta$ cells). Panels labeled DHIC2 2-B4 and DHIC2 2-C12 illustrate staining with antibodies that react with alpha cells, although DHIC2 2-B4 may react to a lesser extent with other pancreatic endocrine cells. Antibodies with duct-specific labeling are illustrated in panels labeled DHIC2 4A-10 and DHIC3 5-H10, and exocrine acinar labeling is shown in HIC1 1-C10. Sections of pancreas were incubated with primary antibodies, then with a Cy-3- or FITC-conjugated detection antibodies. Cells reacting with primary antibody appear light against a dark background of cells that do not react with the antibody.

TABLE 4

Monoclonal Antibodies

| Hybridoma/ Monoclonal Name | Immunoglobulin Isotype | Insulin/ Glucagon | Cell Type Specificity* |
|---|---|---|---|
| HIC0 4-F9 | IgG1 | 0.58 | Pan-islet cells |
| HIC1 2-B4 | ND | 1.23 | Pan-islet cells |
| HIC1 4-G6 | ND | 0.77 | Pan-islet cells |
| HIC1 7-H10 | IgG1 | ND | Pan-islet cells |
| HIC0 3-C5 | IgM | 79 | Endocrine cell subset |
| HIC1 5-F10 | IgG1 | 14 | Pan-islet cells |
| DHIC2 2-B4 | IgG1 | ND | Alpha cells > other islet cells |
| DHIC2 2-C12 | IgM | 0.001 | Alpha cells |
| HIC1 1-C10 | IgM | NA | Exocrine cells |
| DHIC2 4-A10 | IgG1 | NA | Duct cells |
| DHIC3 5-H10 | IgM | NA | Duct cells |

ND; not done. NA; not applicable.
*Cell type specificity defined insulin to glucagons ratio and/or by two color immunohistochemistry.

Example 2

Fluorescent Activated Cell Sorting (FACS)

For the in situ imaging of live beta cells, monoclonal antibodies must react with cell surface molecules on those cells. Flow cytometric analyses of enzyme-dispersed islet cells have revealed that all of the antibodies react with cell surface molecules (see FIG. 2). For this analysis, intact islets obtained from the Islet Cell Resource Centers were dispersed by treatment with trypsin (0.05% for 5-10 min at 37° C.). Enzyme-dispersed islet cells were then incubated with islet cell specific antibodies, and bound primary antibody was assessed by flow cytometry using an APC-conjugated polyclonal anti-mouse immunoglobulin as a secondary reagent. The upper left panel illustrates levels of signal associated with the negative control. The other panels illustrate staining with the eleven antibodies introduced in FIG. 1.

Antibody reactivity with cell surface molecules is revealed by a right shift in the fluorescent signal of a subset of the cells. Positive cells are contained within the box on the right side of each panel, and the percentage of cells identified as positive is indicated in each box. The antibodies produced by the hybridomas HIC0 4-F9, HIC1 2-B4, HIC1 4-G6, HIC1 7-H10, HIC0 3-C5, HIC1 5-F10, DHIC2 2-B4, or DHIC2 2-C12 all react with cell surface molecules on trypsin-dispersed pancreatic endocrine cells. The antibodies produced by hybridomas DHIC2 4A-10 and DHIC3 5-H10 react with cell surface molecules on pancreatic duct-derived cells and antibodies produced by the hybridoma HIC1 1-C10 react with cell surface molecules on exocrine cells.

The INFLUX™ cell sorter is used on a routine basis to viably sort human pancreatic islet cells, although other cell sorters can also be utilized. For sorting of individual islet cells, islets are dispersed by a brief exposure to trypsin (0.05% for 5-10 min at 37° C.).

Sorted and unsorted trypsin-dispersed islet cells were plated for growth. Trypsin-dispersed cells sorted using the INFLUX™ instrument have the same proliferative potential as cells that had not been passed thru the instrument.

In order to stain the human islets with the antibodies disclosed herein, the islets are dispersed into single cell suspensions by incubation with trypsin (0.05% for 5-10 min at 37° C.), isolated cells are washed, and then stained with candidate antibodies (using a fluorchrome-conjugated secondary anti-mouse immunoglobulin). Labeled cells are sorted into islet cell populations that react with the antibody (positive cells) and populations that do not react with the antibody (negative cells). mRNA from these cell populations are subjected to real time polymerase chain reaction analyses using primers specific for insulin (as a beta cell specific marker) and glucagon (as an alpha cell specific marker). The interpretation of these reactivity profiles would be that the candidate antibodies are beta cell specific, alpha cell specific, or labeled both alpha and beta cells, respectively. These data are shown in Table 4.

Example 3

Additional Methods

An alternate method for determining cell specificity of antibodies is to stain cells with test antibodies as described above, then fix and permeabilize the cells and stain for intracellular enzymes, insulin, glucagon, and amylase using polyclonal rabbit antibodies and an alternate fluorochrome for enzyme detection.

A third strategy used to characterize the cellular specificities of these antibodies is two-color fluorescence microscopy. Pancreatic tissue is labelled with candidate mouse antibodies (with a Cy-3-conjugated secondary antibody as in the preliminary data section) and with polyclonal rabbit antibodies directed against enzymes produced by known islet cell subsets (with FITC). In some examples, antibodies that specifically bind glucagon or insulin are used. The anti-enzyme antibodies are obtained form commercial vendors as unconjugated polyclonal antibodies. These antibodies are biotinylated and detected on tissue sections using streptavidin conjugated to FITC. This strategy demonstrates that the antibodies co-label cells producing insulin only, glucagon only, or both enzymes. Thus, the antibodies disclosed herein can readily be identified as beta cell specific, alpha cell specific, or labeled both alpha and beta cells, respectively. Control slides stained for both insulin and glucagon are included in these analyses as a control, as antibodies to these enzymes should not co-label cells. Staining for both enzymes is accomplished with biotinylated antibodies by using the following strategy: 1) incubate with the first biotinylated antibody; 2) wash, then incubate with a streptavidin-fluorochrome conjugate (which will bind to the first antibody); 3) wash and block with free biotin (this step blocks available biotin binding sites on streptavidin); 4) incubate with second biotinylated antibody; and 5) wash, then incubate with a distinct streptavidin-fluorochrome conjugate (which will bind the second antibody).

Example 4

Humanization and Production of an scFv

CDR amino acid sequences from monoclonal antibody HIC0 4-F9 (see Table I) are used for humanization and construction of recombinant scFv and $scFv_2$ fragments. A diagram illustrating the production of humanized antibodies (and scFv) is shown in FIG. 3. The HIC0 4-F9 monoclonal antibody heavy-chain variable domain ($Fv_H$) has significant sequence homology to the humanized Fab D3h44. Thus, the CDRs from HIC0 4-F9 are inserted into the D3h44 framework regions.

Protein-based and cell-based assays have been used extensively for the purpose of evaluating engineered antibodies (reviewed by Qu et al, Methods. 36:84-95, 2005).

Competitive cell-based binding assays are developed to compare the antigen binding capabilities of engineered antibodies with those of the parental mouse monoclonal antibodies. For initial assays, trypsin-dispersed (0.05% for 5-10 minutes at 37° C.) human islets are used as a source of target cells. For these assays, unlabeled engineered antibodies are used as a competitor of antigen binding by phycoerythrin (PE)-labeled parental antibodies. Briefly, dispersed islet cells are plated at $1 \times 10^5$ cells/well in a 96-well plate (100 uL/well). A constant amount of PE-labeled parental antibody (10 nM) is mixed with varying concentrations of unlabeled parental or engineered antibodies (0.2-1,000 nM) and added to each well (100 uL/well), with each experimental condition set up in triplicate. Plates are preblocked to prevent binding of PE-conjugated antibody to the plate surface (phosphate buffered saline (PBS), 0.05% Tween 20, and 5% fetal calf serum (FCS) for 2 hours at room temperature). After adding cells plus antibodies, the plates are incubated on ice with gentle mixing for 2 hr. Plates are then centrifuged and washed five times to eliminate unbound PE-labeled antibody and evaluated for PE signal using a fluorescence plate reader. The fluorescence associated with cells is plotted versus the concentration of unlabeled antibodies, yielding competitive inhibition curves. Successful engineering results in similar curves for the engineered and parental antibodies. Competitive radio-immunoassays can also be used as an alternative for this determination.

Example 5

Identification of Protein Antigens and Development of Assays

Immunoaffinity column chromatography are used to isolate/enrich beta cell associated target antigens (Nakache et al., Nature 337:179-181, 1989). The enriched material is run on 1D SDS PAGE gels, and bands corresponding to immunoreactive species (determined by Western Blot of duplicate gels) is excised, subjected to tryptic digestion, and analyzed by nanoLC/MS/MS. Briefly, gel slices are washed to remove coomassie stain and then dehydrated by the addition of neat acetonitrile (ACN). Gel slices are treated with DTT and iodoacetamide to reduce and alkylate cystines. Prior to proteolysis, the gel slices are washed and dried again. Proteolysis with trypsin is carried out overnight at 37° C., and peptides are extracted from the gel slices by the addition of two aliquots of 1% formic acid.

Protein identification and quantification is carried out using an Applied Biosystems Qstar XL. Briefly, 5 uL of peptides from the digest is injected onto a reverse phase trap column, washed thoroughly, and then switched in-line with a 15 cm×75 uM analytical column packed with C18 reverse phase material. Peptides are eluted with an increasing organic gradient (0-40% ACN) and introduced to the mass spectrometer via an electrospray interface. Data dependent acquisition is used to select precursor ions and set collision energy for collisionally induced dissociation (CID) of the three most abundant ions derived from each survey scan. Product ion spectra is used to obtain protein identification via database searching using the MASCOT™ (Matrix science) search engine.

Candidate antigen gene sequences are identified using GenBank and those sequences are used to design primers for extracellular domain sequence amplification. Type I proteins are expressed as human IgG1 Fc constructs and Type II proteins are expressed with an N-terminal Flag tag. Fusion proteins are detected and purified by their tags.

Extracellular domains of proteins of interest are amplified by PCR from beta cell cDNA. Type I membrane proteins is cloned into a pCR-3 mammalian expression vector (Invitrogen) modified to include the following features: 1) a multiple cloning site for insertion of the extracellular domain of the protein; and 2) a cassette encoding the hinge, CH2 and CH3 domains of human IgG1 (GENBANK® accession number X70421, as available on Apr. 17, 2006). Extracellular domains of Type II membrane proteins are cloned into a pCR-3 vector modified to provide the following elements: 1) the signal peptide of heamagglutinin to target the recombinant protein to the secretory pathway, 2) the eight amino acid Flag sequence, 3) a linker sequence located between the Flag tag and the ligand and multiple cloning sites for the insertion of cDNA.

Beta cell cDNA are amplified with a high fidelity DNA polymerase, and the PCR product is cloned into a pCR-blunt vector for sequencing. The cDNA is recloned into the appropriate PCR-3 modified expression vectors and used for either transient expression using 293T cells or stable expression by HEK293 (ATCC CRL 1573). Fc-chimeric proteins are purified using a protein A column (Pierce), while Flag-tag recombinant protein are purified on an M2-agarose (Sigma) column.

Competitive protein-based binding assays are developed to compare the antigen binding capabilities of any humanized forms of the antibodies disclosed herein with those of the parental mouse monoclonal antibodies. For these assays wells of 96-well plates are coated with target antigen (target antigen at a concentration of 1 ug/mL in 50 uL of PBS). The plates are then blocked to prevent binding of PE-conjugated antibody to plastic (PBS, 0.05% Tween 20, and 5% FCS for 2 hr at room temperature). After completion of the blocking step, a constant amount of PE-labeled parental antibody (10 nM) is mixed with varying concentrations of unlabeled parental or engineered antibodies (0.2-1,000 nM) and added to each well (100 uL/well), with each experimental condition set up in triplicate. The plates is incubated on ice with gentle mixing for 2 hours, plates are washed 5 times to eliminate unbound PE-labeled antibody and evaluated for PE signal using a fluorescence plate reader. The fluorescence associated with the wells is plotted versus the concentration of unlabeled antibodies, yielding competitive inhibition curves. Successful engineering results in similar curves for the engineered and parental antibodies.

Example 6

Imaging of Pancreatic Beta Cells in an Animal Model

The use of the monoclonal antibodies disclosed herein for imaging can be assessed using immunodeficient mice transplanted with human islets (see Moore et al., Diabetes. 2001; 50:2231-2236). Islets are transplanted into immunodeficient NOD-SCID mice (Fowler et al., Transplantation 79:768-776, 2005). Briefly, human islets (500-2,000 per animal/per tissue site) are transplanted into these mice at ~48 hours following pancreas dissociation. Islets are delivered to two sites, the liver by injection into the portal vein, and the kidney by injection between the capsule and the renal parenchyma. At 4 and 8 weeks post islet transplant, time points when transplanted islets are well vascularized, candidate beta cell specific imaging reagents are injected intravenously (iv) into transplant recipient animals. Animals receive graded doses (10 ug, 1 ug, 0.1 ug, or 0.01 ug) of imaging reagents in a volume of 50 uL, and at 12 and 24 hr after reagent injection, animals are euthanized and liver and kidney is recovered and evaluated for presence of the imaging reagents and specific association of those reagents with transplanted beta cells. The injected imaging reagents are FITC-conjugated, PE-conjugated, and biotin-conjugated. Controls include: Parental antibodies; antibodies with specificities unrelated to islets; and engineered antibodies that lack specificity for human beta cells.

Tissues recovered from mice receiving candidate imaging reagents or control reagents are processed for tissue section analyses and flow cytometric analyses. High resolution studies of beta cell targeting by injected imaging reagents are conducted by evaluating sections from frozen tissue. For these analyses, thin (5 um) sections of frozen tissue are fixed in acetone, stained as required, and evaluated by fluorescence microscopy. With reagents labeled with FITC or PE, no additional staining is required for detection. For sections containing reagents labeled with biotin, incubation with streptavidin-FITC, -PE or alternate streptavidin conjugate is required for detection. Biotinylated reagents are used to allow for greater flexibility in designing detection schemes and because biotin-streptavidin (or biotin-avidin) detection systems allow for substantial signal amplification. Although islets are easy to detect in H&E stained sections, sections can also be stained with antibodies to human insulin and to human HLA Class I molecules to precisely localize human beta cells and human islets, respectively. These antibodies are labeled with fluorochromes distinct from those used to identify candidate imaging reagents, to allow detection of beta cell imaging reagent (the engineered antibodies), beta cells (insulin expressing) and islet cells (HLA Class I expressing) within the same tissue section.

Islets transplanted under the kidney capsule can be readily dissociated, by micro-dissection, from renal parenchyma. Following recovery, these islets are enzymatically dispersed using trypsin (0.05% for 5-10 minutes at 37° C.) and evaluated by flow cytometry. Detection strategies for engineered imaging reagents, beta cells, and islet cells are similar to those described above. However, cells are permeablized to allow detection of insulin or internalized biotinylated imaging antibody.

Example 7

General Methods

Larger Scale Antibody Preparations. For larger scale antibody preparations, hybridomas are grown in serum-free media (Hybridoma-SFM; Gibco). Hybridoma growth in this media generally yields antibody at a concentration of 5-20 mg/L. Following exhaustion of cultures, antibody is recovered/purified from culture supernatant using immobilized protein G (Pierce; as per manufacturer's instructions; http://www.piercenet.com/). Protein G works well for the isolation of most mouse immunoglobulin isotypes. Concentration/size exclusion chromatography is used for mouse IgM.

Immunoaffinity Isolation of Beta Cell Antigens. Beta cell antigens are immunoaffinity purified from triton X-114 lysates of pancreatic islets using AminoLink affinity columns obtained from Pierce and used as per manufacturer's instructions (available on the internet, see the Pierce website). Briefly, purified monoclonal antibodies targeting cell surface molecules on pancreatic beta cells are covalently linked to AMINO LINK™ coupling gel columns. Then remaining active sites on the columns are blocked and the columns washed. Columns are then equilibrated and antigen-containing sample is applied. Columns are then incubated to allow maximal binding of beta cell antigen, washed to remove undesirable materials, and treated with elution buffer to promote release of bound antigen. Antigen containing solution is then neutralized, the buffer is exchanged to an appropriate working or storage buffer.

Antibody/Protein Labeling. To facilitate studies using more than one antibody or where directly conjugated antibody is desirable, purified antibodies are conjugated to biotin and/or different fluorochromes (R-Phycoerythrin and NHS-Fluorescein). These fluorochromes have distinct emission spectra and can therefore be distinguished when used together. NHS-LC-biotin is used for antibody biotinylation and offers the potential for signal amplification and/or the use of additional fluorochromes (as avidin or streptavidin conjugates). The fluorochromes and biotin are obtained from Pierce, and are used as per manufacturer's instructions (available on the internet at the Pierce website). By using antibodies labeled with different fluorchromes, tissue sections, cell lines, enzymatically dispersed cells, or intact islets can be stained with two or more antibodies at the same time.

Example 8

Method for the Isolation of Pancreatic Endocrine Cells

There is a need to provide a means for the isolation of large numbers of pancreatic endocrine cells or pancreatic endocrine-like cells, derived from donor tissue or from ex vivo culture. Paramagnetic bead separation, using the monoclonal antibodies disclosed here, can be employed to separate large numbers of pancreatic endocrine cells. For this analysis, intact islets obtained from a pancreas, such as a human cadaveric pancreas, or culture derived islet-like cells are dispersed by treatment with trypsin (0.05% for 5-10 minutes at 37° C.).

Enzyme-dispersed cells are then incubated with a combination of monoclonal antibodies. Cells with associated monoclonal antibodies are incubated with anti-mouse immunoglobulin-coated paramagnetic beads. The cells targeted by the monoclonal antibodies are bound to the paramagnetic beads and are separated from the cells that are not bound by the beads using a magnet. Cells not attracted to the magnet are removed by washing the cells while exposed to the magnet. Cells attracted to the magnet are retained in the magnetic field. Upon removal from the magnetic field, paramagnetic bead associated cells are recovered.

In one protocol, to achieve maximum purity, rounds of negative selection (by collection of cells which were not retained on the column after labeling with markers of duct or exocrine identity) are followed by a round of positive selection (by collection of cells which were retained on the column after labeling with markers of endocrine identity). An example is the depletion of cells labeled by DHIC2 2-C12, HIC1 1-C10 or DHIC3 5-H10 (markers of alpha cell, exocrine cell, and duct cell identity) and then positive selection for cells labeled with HIC1 2-B4 (pan-endocrine). The result is a pure population of beta cells.

Alternatives to the indirect separation strategy detailed above include use of paramagnetic beads coated with the pancreatic endocrine specific monoclonal antibodies described herein, or avidin- or streptavidin-coated paramagnetic beads. When avidin- or streptavidin-coated beads are used, the pancreatic endocrine specific monoclonal antibodies need to be biotinylated. Thus, the antibodies disclosed herein can be used to isolate pancreatic endocrine cells.

Example 9

Method for the Ex Vivo Generation of Pancreatic Endocrine Cells

The antibodies disclosed herein can also be used to distinguish between useful and contaminating cells in cultures intended to produce beta-like or endocrine-like cells. A variety of different cell sources and/or culture environments may provide beta-like or endocrine-like activities, and these antibodies can be used to select for these characteristics.

For example, cells of interest can be produced in vitro by culturing human cadaveric islets; these cultures are epithelial-to-mesenchymal-transition (EMT) cultures. These cultures are established using human islet cell preparations, and yield large numbers of cells with a detectable level of glucose-responsive insulin secretion (see Gershengorn et al., supra, 2004). The islets and/or cells can be isolated from a pancreas obtained from a cadaver using the antibodies disclosed herein. In another instance, non-islet exocrine cells may be cultured and induced to adopt an endocrine phenotype (see Todorov et al., Pancreas 32(2):130-138, 2006). The appropriate input populations for these cultures can be determined and obtained by positive or negative labeling of live cells using the antibodies described here. An example of the differential potential of pancreatic subpopulations that can be discriminated using these antibodies is illustrated in FIG. 3 and Table 5. Isolation of HIC1 7-H10$^{hi/+}$ cells from a mesenchymal phase culture derived from human islets prior to the mesenchymal-to-epithelial transition resulted in a more complete transition (as assessed morphologically) and an enhanced level of insulin expression. Although cell lines established with islets from different patients or by different methodologies may exhibit distinct characteristics (for example, in some cases the HIC1 7-H10$^{low/-}$ cells could be the more productive population), these antibodies can be used to obtain either population. Regardless of the tissue of origin, the output cells from these cultures can be selected using the antibodies disclosed herein. Thus, viable pancreatic endocrine cells are purified using the antibodies disclosed herein.

TABLE 5

Cell culture to generate insulin-expressing cells

| Sorted sub-population from EMET culture | Mesenchymal phase fold expansion (1 w) | Islet-like cluster formation efficiency* | Insulin mRNA expression in ICAs (relative to unsorted) |
|---|---|---|---|
| HIC1 7-H10$^{hi/+}$ | 58x | High | 251x |
| HIC1 7-H10$^{low/-}$ | 23x | None/Very low | N/A |

N/A: Not applicable
*Judged by the proportion of cells which formed spheroid cultures associated with epithelial transition It is estimated that a diabetic subject will need at least about 10,000, or between 5,000 and 30,000 islets per kilogram body weight (or a equivalent number of pancreatic endocrine cells) per transplantation to have a substantial beneficial effect from the transplantation. In one specific, non-limiting example the cells are administered by sub-cutaneous injection, or by implantation under the kidney capsule, through the portal vein of the liver, or into the spleen. If, based on the method of administration, cell survival after transplantation in general is low (5-10%) additional islets, such as up to 100,000 islets per kilogram body weight, are transplanted.

Transplantation can be achieved by injection. Injections can generally be made with a sterilized syringe having an 18-23 gauge needle. For example, a pancreatic endocrine cell suspension or islets is transplanted using a needle not bigger than 1 mm in diameter. The cells are administered by subcutaneous injection, intra-peritoneal injection, injection under the kidney capsule, injection through the portal vein, and/or injection into the spleen. The cells can be encapsulated prior to administration, such as by co-incubation with a biocompatible matrix known in the art. A variety of encapsulation technologies have been developed (e.g., Lacy et al., *Science* 254:1782-84, 1991; Sullivan et al., *Science* 252:7180712, 1991; WO 91/10470; WO 91/10425; U.S. Pat. No. 5,837,234; U.S. Pat. No. 5,011,472; U.S. Pat. No. 4,892,538, each herein incorporated by reference).

The cells can be implanted using an alginate-polylysine encapsulation technique (O'Shea and Sun, *Diabetes* 35:943-946, 1986; Frischy et al., *Diabetes* 40:37, 1991). In this method, the cells are suspended in 1.3% sodium alginate and encapsulated by extrusion of drops of the cell/alginate suspension through a syringe into CaCl$_2$. After several washing steps, the droplets are suspended in polylysine and rewashed. The alginate within the capsules is then reliquified by suspension in 1 mM EGTA and then rewashed with Krebs balanced salt buffer. Each capsule is designed to contain several hundred cells and have a diameter of approximately 1 mm. Capsules containing cells are implanted intraperitoneally and blood samples taken daily for monitoring of blood glucose and insulin.

Example 10

Use of Monoclonal Antibodies to Isolate Cells for Use in a Bioartificial Pancreas There is a need to provide a biocompatible and implantable device containing islets of Langerhans, or the insulin producing β cells, that can supply the hormone insulin for the purpose of controlling blood glucose levels in people with diabetes mellitus requiring insulin. Insufficient regulation of blood glucose levels in people with diabetes has been associated with the development of long-term health problems such as kidney disease, blindness, coronary artery disease, stroke, and gangrene resulting in amputation. Therefore, there is a need to replace conventional insulin injections with a device that can provide more precise control of blood glucose levels.

Many modalities are currently available to replace the impaired pancreatic beta cell function in diabetes mellitus patients. The electromechanical modality utilizes insulin delivery systems that release insulin in response to blood glucose levels that are continuously measured via a glucose sensor. Difficulties with the sensors led to the development of programmed insulin delivery via a continuous perfusion pump. This approach however also falls short of the in vivo regulation, i.e. the regulation of insulin secretion by glucose and its modulation by several hormonal and neuronal factors.

To overcome these problems, bioartificial pancreases have been developed. These systems separate the transplanted tissue from the diabetic recipient by an artificial barrier, which diminishes immune rejection, yet allows the transfer of the glycemic signal from the blood to the islet cells and the transfer of the pancreatic hormones from the islet cells to the blood. An artificial pancreas accomplishes this by having a selectively permeable barrier, which is permeable to glucose and insulin, but not to immunoglobulins and immunocytes. Artificial pancreas devices work based on the transfer through the membrane of a glycemic signal from blood to the pancreatic endocrine cells, and insulin from the pancreatic endocrine cells to the recipient. In one embodiment, the pancreatic endocrine cells are in the form of islets.

In general, the transfer of a substance from one compartment to the other across a membrane can be achieved either by diffusion, dialysis, or by convection, ultrafiltration or a combination of these methods. Artificial pancreases are generally divided among those that utilize diffusion mechanisms, those that utilize convection mechanisms, or those that utilize a combination of both mechanisms. Diffusion represents the transfer of the substance itself without transfer of the solvent. Convection, in contrast, involves the transfer of the solvent and any molecules dissolved therein as long as they are smaller than the pores of the membrane.

Suitable devices for use with pancreatic endocrine cells as an artificial pancreas are well known in the art. Specific, non-limiting examples devices of use are disclosed in U.S. Pat. No. 5,741,334; U.S. Pat. No. 5,702,444; U.S. Pat. No. 5,855,616; U.S. Pat. No. 5,913,998; U.S. Pat. Nos. 6,023,009; and 6,165,225, all of which are incorporated by reference herein.

Thus, the antibodies disclosed herein can be used to isolate pancreatic endocrine cells. These cells are then included in a device as a bioartificial pancreas, and the bioartificial pancreas is then implanted into a subject. The implantation of the bioartificial pancreas results in the treatment of a disorder. In embodiment, the implantation of the bioartificial pancreas results in the treatment of diabetes.

Example 11

Antibodies that Specifically Bind Pancreatic Ductal Cells

Figure 5:
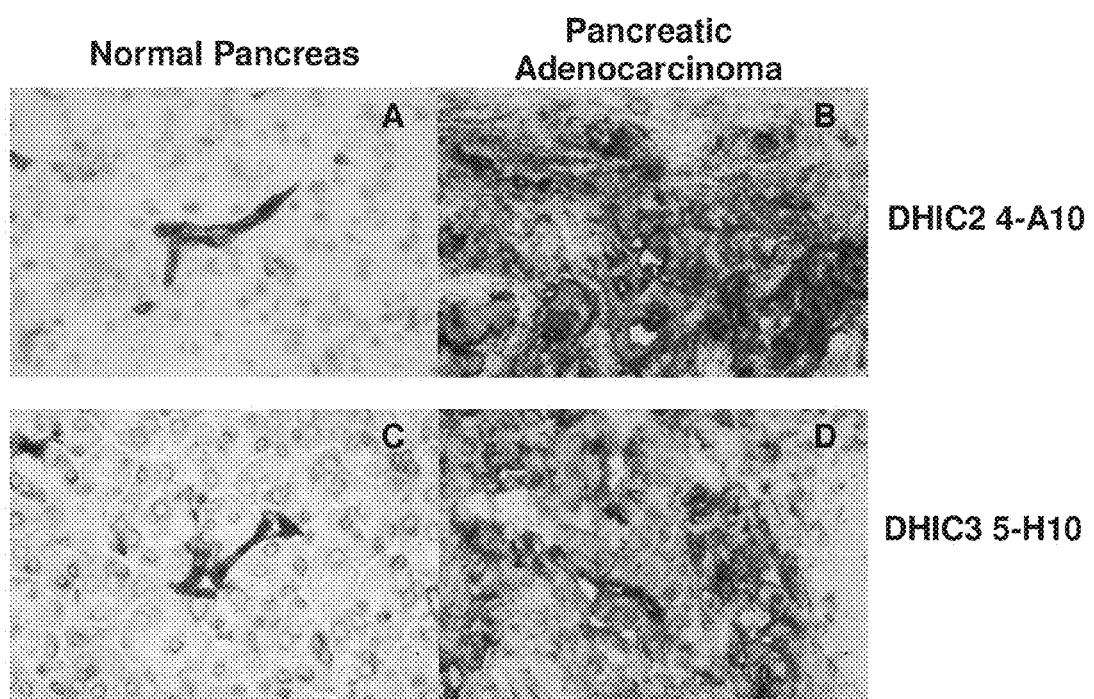
FIG. 5 is a set of digital images obtained using monoclonal antibodies that specifically bind antigens associated with pancreatic duct cells and pancreatic adenocarcinoma cells. The monoclonal antibodies DHIC2 4-A10 and DHIC3 5-H10 were incubated with sections of normal pancreas (left panels) and pancreatic adenocarcinoma (right panels), and a peroxidase-conjugated polyclonal secondary antibody was used to detect section-bound unlabeled primary antibody. Addition of the chromogen 3,3'-diaminobenzidine tetrahydrochloride (DAB) allowed visualization of bound antibody (dark gray to black) as well as areas where with no antibody binding (light areas). Stained sections were analyzed by light microscopy.

Multiple monoclonal antibodies that meet the criteria of staining normal duct epithelium and pancreatic adenocarcinoma cells have been identified. FIG. 5 illustrates two independently derived monoclonal antibodies with this specificity profile. Reactivity with normal duct epithelium is shown in panels A and C, while extensive reactivity with pancreatic adenocarcinoma cells is shown in panels B and D. For the results illustrated in this figure, supernatants from hybridomas were tested on acetone or methanol fixed frozen human pancreas sections (either normal pancreas or pancreatic adenocarcinoma), and a peroxidase-conjugated polyclonal secondary antibody was used to detect section-bound unlabeled primary antibody. Addition of the chromogen 3,3'-diaminobenzidine tetrahydrochloride (DAB) allowed visualization of bound antibody (dark staining) against a light background of cells that were not bound by antibody. Stained sections were analyzed by light microscopy.

In addition to characterization on specimens of normal and neoplastic pancreas, the two antibodies illustrated in FIGS. 1 and 5 have been evaluated on a variety of additional tissues (summarized in Table 6).

TABLE 6

Cell and Tissue Distribution of Duct Reactive Antibodies.

| | Antibody Designation | |
|---|---|---|
| Tissue | DHIC2 4-A10 | DHIC3 5-H10 |
| Normal | | |
| Pancreas | + (Duct epithelium) | + (Duct epithelium) |
| Liver | + (Duct epithelium) | + (Duct epithelium) |
| Breast | − | − |
| Kidney | − | − |
| Ovary | − | − |
| Stomach | ND* | − |
| Neoplastic | | |
| Pancreatic adenocarcinoma | + | + |
| Liver cholangiocarcinoma | + | + |
| Ovarian cholangiocarcinoma | ND | + |
| Liver hepatocellular carcinoma | − | − |
| Breast adenocarcinoma | − | − |
| Stomach adenocarcinoma | + | + |
| Lung adenocarcinoma | + | + |
| Kidney carcinoma | − | − |
| Ovarian Endocarcinoma | ND | − |
| GIST | − | − |
| Leiomyosarcoma | − | − |

*ND, not determined

The results with monoclonal antibodies DHIC2 4-A10 and DHICH3 5-H10 suggest that duct cells in diverse tissues exhibit tissue-selective marker expression profiles (for example, these two antibodies react with markers on pancreatic and liver duct cells, but they do not react with duct cells in mammary gland). Staining of adenocarcinomas derived from different tissues indicates that adenocarcinomas also exhibit distinct marker profiles (for example, these antibodies react with pancreatic adenocarcinoma and do not react with breast adenocarcinoma or liver hepatocellular carcinoma). The results suggest that these antibodies are of use in the diagnosis of pancreatic adenocarcinoma.

Figure 2:
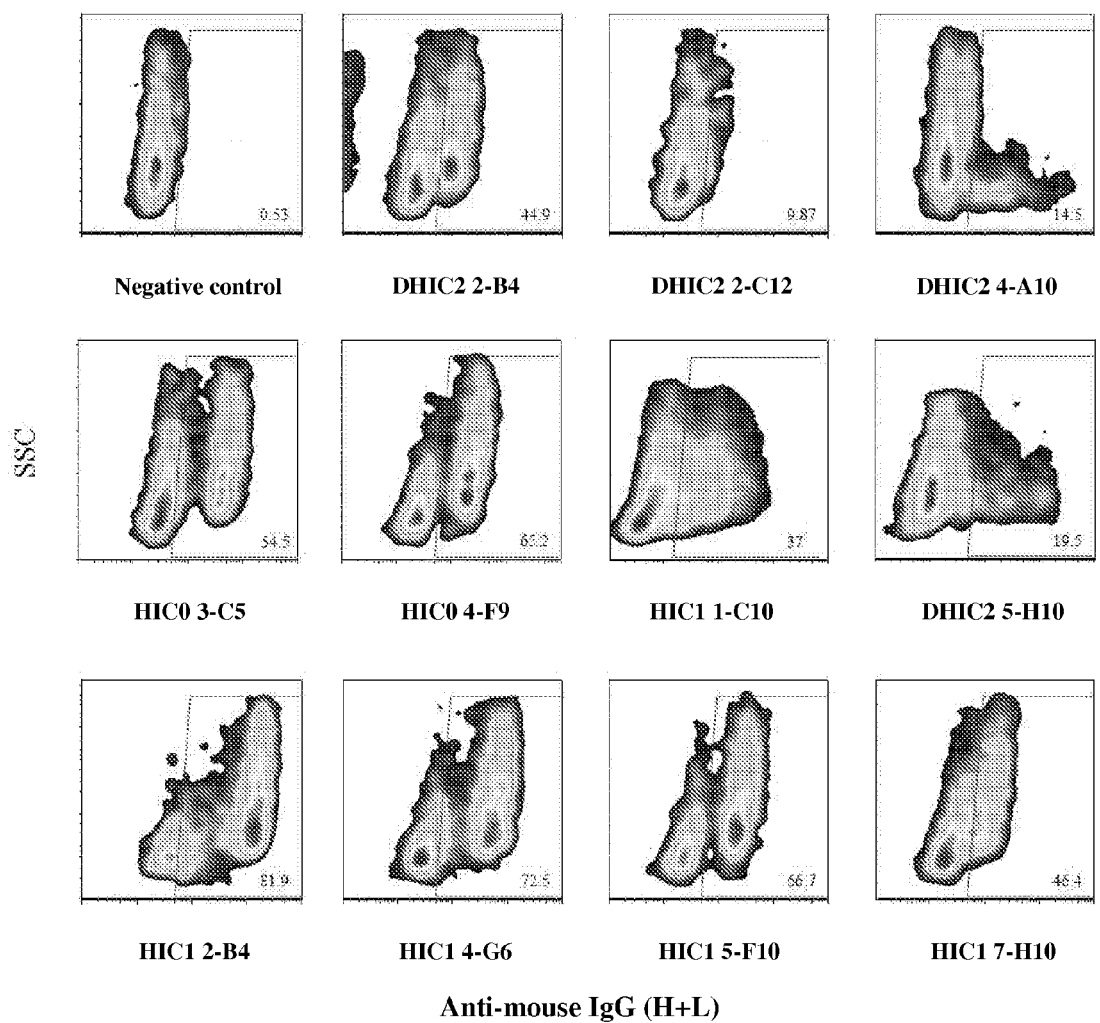
FIG. 2 is a set of plots showing that antibodies directed against pancreatic cells react with cell surface molecules. Flow cytometric analyses of viable (non-fixed) enzyme-dispersed pancreatic cells revealed that all of the antibody-producing hybridomas react with cell surface molecules. Enzyme-dispersed pancreatic cells were incubated with pancreatic cell specific antibodies, and antibody reactivity was assessed by flow cytometry using an APC-conjugated $F(ab')_2$ fragment anti-mouse immunoglobulin (H+L).

The cell surface reactivity profiles of the two duct-reactive antibodies is illustrated in FIG. 2. For this analysis, pancreatic cells (enriched for islet content—see figure legend) obtained from the Islet Cell Resource Centers were dispersed by treatment with trypsin (0.05% for 5 min). Enzyme-dispersed cells were then incubated with candidate antibodies and bound primary antibodies were assessed by flow cytometry using APC- or PE-conjugated polyclonal immunoglobulin as a secondary reagent. The left panels illustrate levels of signal associated with the negative controls, and right panels illustrate cell surface staining with duct reactive antibodies. These data demonstrate cell surface expression of antigens recognized by these two antibodies on roughly 10% of cells within the pancreatic cell preparation.

Pancreatic ductal adenocarcinoma is the most lethal of human solid cancers. Although the incidence of this cancer is relatively low at approximately 32,000 newly diagnosed cases per year in the USA (Jemal, Cancer statistics, CA Cancer J. Clin. 2005; 55:10-30, 2005), the current five-year survival rate following initial diagnosis is 1-5% (see Wray et al, Gastroenterology 128:1626-1641, 2005). As a consequence of the high mortality rate for patients with pancreatic adenocarcinoma, this cancer is the fourth leading cause of cancer-related deaths for men and the fifth leading cause of cancer-related deaths for women in the USA (see Wingo et al., Cancer 97:3133-3275, 2003). Despite continuing substantive efforts to alter the disease course in patients with pancreatic adenocarcinoma, conventional therapies including radiation and/or chemotherapy have had little impact on this aggressive disease (Hawes et al., Am J. Gastroenterol. 95:17-31, 2000). At present, tumor resection during early stage disease is the only potentially curative option for these patients (Sener et al., J Am Coll Surg. 189:1-7, 1999).

A primary reason for the low survival rate for patients with pancreatic adenocarcinoma is the inability to diagnose this cancer during early stage disease. At present, most patients are diagnosed with advanced disease, with only 15% of newly diagnosed patients presenting with localized operable cancer (Li et al, Lancet 363:1049-1057, 2004). As the inability to detect this cancer at early stages is viewed as a significant barrier to the effective treatment of these patients, there is substantial interest from the research community, in defining new markers of early disease. The survival rate for patients with pancreatic adenocarcinomas is also negatively impacted by the lack of effective therapies. Long-term survival of patients undergoing resection of localized operable tumors is approximately 20% (see for example, Schmidt et al., Arch Surg. 139:718-725 and 725-717, 2004). Thus, the development of novel therapies is also viewed as critically important for successful disease management.

Most patients diagnosed with pancreatic adenocarcinoma have a life expectancy of months rather than years. The poor prognosis for these patients is due to 1) the inability to detect early stage disease, 2) the metastasis of these tumors to distant sites early during the course of this disease, and 3) the resistance of the disease to conventional chemotherapy and/or radiation therapy. For patients with tumors located in the head and body of the pancreas, symptoms of disease are associated with compression of the bile duct, the pancreatic duct, the mesenteric and celiac nerves, and the duodenum (Evans D B A J, Willett C G. Cancer of the pancreas. Philadelphia: Lippincott, Williams & Wilkins; 2001); and these tumors may or may not cause the patient pain. For tumors located in the tail of the pancreas, patients may have pain on the left side of the abdomen, but pain is generally associated with late stage disease. Thus, patients with pancreatic adenocarcinoma do not generally seek treatment during early stage disease.

As patient survival clearly depends on early detection of this disease, there is tremendous interest in the identification of markers that can be used for disease detection and diagnosis. Candidate serum markers of disease include: the sialylated Lewis[a] blood group antigen CA19-9 (see Gupta et al., Cancer 56:277-283, 1985), macrophage inhibitory cytokine-1 (MIC-1; also known as placental TGF-beta (Moore et al., J Clin Endocrinol Metab. 85:4781-4788, 2000), prostate-derived factor (Karan et al., Biochem Biophys Res Commun. 305:598-604, 2003), and growth/differentiation factor 15 (Koniaris, J Gastrointest Surg. 7:901-905, 2003); and osteopontin (Kolb et all, Cancer Biol Ther. 4:740-746, 2005). Of these markers, CA19-9 has been the most widely studied. Unfortunately, the results from those studies do not support the use of this marker in disease detection and diagnosis, particularly in the diagnosis of early disease, where a high frequency of patients test negatively for CA19-9 (Sawabu et al., Pancreas 28:263-267, 2004). In addition to the false-negative results associated with detection of early disease, false-positive results are obtained at high frequency in patients with acute cholangitis (Albert et al., Dig Dis Sci. 33:1223-1225, 19888) and chronic pancreatitis (Furuya et al., Br J Cancer 73:372-376, 1996). Current data suggest that MIC-1 may be a better marker of pancreatic adenocarcinoma than CA19-9 (Koopmann et al., Clin Cancer Res. 10:2386-2392, 2004). However, MIC-1 is also present at high frequency in patients with pancreatitis (Koopmann et al., supra). Osteopontin has also not allowed robust detection of disease (Kolb et al., Cancer Biol Ther. 4:740-746, 2005) Thus, there is currently no serum marker than can be used to accurately detect and diagnose early stage pancreatic adenocarcinoma.

One treatment for patients with advanced pancreatic adenocarcinoma is the chemotherapeutic agent gemcitabine (Burris et al., J Clin Oncol. 15:2403-2413, 1997). This drug is a nucleoside analogue that inhibits cell division, by interfering with DNA and RNA synthesis, and yields a modest improvement in survival and clinical benefit (Burris et al, supra). The drug combination of gemcitabine administered in combination with erlotinib (Tarceva) may have activity in advanced disease. Tarceva is a small molecule that targets the epidermal growth factor receptor 1 (EGFR) pathway and inhibits tyrosine kinase signaling (Ciardiello et al, Clin Cancer Res. 7:2958-297, 2001). In a phase III multi-center study involving 569 patients, patients treated with Tarceva plus gemcitabine exhibited an improvement in overall survival of 23% when they were compared to patients receiving gemcitabine plus placebo (Moore et al., ASCO Annual Meeting, Abstract #1; 2005), and after one year of treatment, 23% of patients receiving Tarceva plus gemcitabine were alive while only 17% of patients receiving gemcitabine plus placebo were alive. Thus, this combination of agents appears to offer an incremental improvement in outcomes in patients with advanced disease.

An alternate strategy to overcome pancreatic adenocarcinoma is by using monoclonal antibodies. One such monoclonal antibody, cetuximab, a humanized monoclonal antibody directed against the EGFR has completed phase II trials and shows promise in patients with EGFR positive pancreatic adenocarcinoma. This antibody blocks activation of the EGFR tyrosine kinase, and effectively blocks the mitogenic signal delivered by ligand binding of this receptor. In the phase II trial, patients were given cetuximab and gemcitabine, and at 1 year, patients who received the combination therapy had an overall survival rate of 31.7% and a progression fee survival rate of 12% (Xiong et al., J Clin Oncol. 22:2610-2616, 2004). This compares favorably with an overall survival rate of 18% and a progression fee survival rate of 9% from a previous phase III trial using gemcitabine alone (Burris et al., J Clin Oncol. 15:2403-2413, 1997). A second monoclonal antibody, avastin, is also being investigated in patients with pancreatic adenocarcinoma. This monoclonal antibody, directed against the VEGF receptor, yielded a 1 year survival rate of 29% when administered with gemcitabine (Kindler et al, Bevacizumab (B) plus gemcitabine (G) in patient (pts) with advanced pancreatic cancer (PC): Updated results of a multi-center phase II trial. Annual Meeting Proceedings (Post-Meeting Edition) Vol 22, No 14S (July 15 Supplement), 2004: 4009, 2004). A phase III trial has been initiated to validate results of the phase II study. The monoclonal antibodies disclosed herein can be used with any of these treatment modalities described above.

Example 12

Additional Studies

Serum and pancreatic duct fluid specimens are evaluated from patients with pancreatic adenocarcinoma for the presence of tumor antigen. For this series of tests, serum and duct fluid specimens are evaluated from 20-30 pancreatic cancer patients using Western blot analyses. Antibody reactivity with a minimum of 10 serum specimens from normal donors (negative controls) is also assessed. Duct fluid from organ donors (from normal donors and from donors with pancreatitis) can also be assessed. The fluid is a negative duct fluid control. Blood samples (10 mL) for preparation of serum is obtained and serum is aliquoted and stored at −80° C. until used. Pancreatic ductal fluid is obtained from cancer patients during pancreatic resection for cancer. This is mixed with a complete mini-protease inhibitor (Roche), aliquoted and stored at −80° C. until used.

There is a growing body of literature on the detection of cancer cells in peripheral blood (see for example, Hayes et al., Clin Cancer Res. 12:4218-24, 2006). The detection of circulating cancer cells can be used for the assessment of tumor cell tumorigenic potential or the responsiveness of particular cancers to candidate therapeutic agents. As the antibodies described herein have been shown to react with cell surface molecules, they are ideally suited for assessment and sorting of circulating live tumor cells from patients with pancreatic adenocarcinoma. Circulating cancer cells are present at low frequencies, ranging from 1 in $10^3$ to 1 in $10^7$ white blood cells. To determine whether pancreatic adenocarcinoma cells are present in peripheral blood, flow cytometry and RT-PCR can be utilized. The detection, quantitation, and isolation of rare cells from peripheral blood requires a multi-step preparative process. Briefly, patient blood is collected in tubes containing an anti-coagulant (lithium heparin or sodium citrate). Red blood cells are lysed using an red blood cell lysis buffer (eBiosciences). Ficoll is not used, as it may result in loss of rare cells in the red blood cell pellet. Cells remaining following red blood cell lysis are stained with a Fluorescein Isothyocyanate (FITC)-conjugated antibody directed against CD45 (a marker expressed on all hematopoietic cells and not on adenocarcinoma cells), with R-Phycoerythrin (PE)-conjugated antibodies directed against adenocarcinoma cells (to detect cancer cells), and with propidium iodide (PI; a DNA-binding dye that reacts with dead cells). When the cells are analyzed or sorted, most cells are excluded from the analysis as they are PI positive (dead) or FITC positive (hematopoietic cells). Cells that do not stain with PI or FITC are assessed for the presence of PE. Cells that are PI negative, FITC negative, and PE positive are sorted as candidate circulating cancer cells. A cancer origin of the cells is confirmed using RT-PCR, where sorted cells are evaluated for the presence of cytokeratin 19 mRNA. Controls include isotype control antibodies and peripheral blood from normal donors.

Example 13

Protein Identification by Proteomic Analyses and Additional Methods

Immunoaffinity column chromatography are used to isolate/enrich the target protein (Nakache et al, Nature 337:179-181, 1989). Briefly, monoclonal antibodies at concentrations of 1-5 mg/mL are covalently coupled to an agarose matrix (AminoLink gel; Pierce; as per the manufacturer's instructions). This material is used as the affinity matrix for column-based immunoaffinity purification of antigen. For antigen purification, cell or tissue lysates containing target antigens are loaded onto these columns at neutral pH, columns are washed to eliminate contaminating proteins, and target antigens are eluted by adjusting the buffer pH to ~2.8. Elution fractions containing target antigen are identified by dot blot analyses.

Column enriched protein antigens are run on 1D SDS PAGE gels, and bands corresponding to immunoreactive species (determined by Western Blot of duplicate gels) are excised, subjected to tryptic digestion, and analyzed by nanoLC/MS/MS. Briefly, gel slices are washed to remove coomassie stain and then dehydrated by the addition of neat acetonitrile (ACN). Gel slices are treated with DTT and iodoacetamide to reduce and alkylate cystines, and prior to proteolysis, the gel slices are washed and dried again. Proteolysis with trypsin is carried out overnight at 37° C. Peptides are extracted from the gel slices by the addition of two aliquots of 1% formic acid.

Protein identification and quantification is carried out using an Applied Biosystems Qstar XL. Briefly, 5 ul of peptides from the digest are injected onto a reverse phase trap column, washed thoroughly, and then switched in-line with a 15 cm×75 uM analytical column packed with C18 reverse phase material. Peptides are eluted with an increasing organic gradient (0-40% ACN) and introduced to the mass spectrometer via an electrospray interface. Data dependent acquisition is used to select precursor ions and set collision energy for collisionally induced dissociation (CID) of the three most abundant ions derived from each survey scan. Product ion spectra is used to obtain protein identification via database searching using the MASCOT™ (Matrix science) search engine.

Large scale production of antibodies are accomplished by growing hybridoms in the CELLLINE™ System (BD Biosciences) using serum-free low protein media (Hybridoma-SFM; Gibco). These cultures generally yields antibody at concentrations of 2-20 milligrams/mL, with contaminating proteins present in the low microgram/mL range (such that the antibodies are usually >98% pure).

It will be apparent that the precise details of the methods or compositions described may be varied or modified without departing from the spirit of the described invention. We claim all such modifications and variations that fall within the scope and spirit of the claims below.

The invention claimed is:

1. An isolated monoclonal antibody comprising a heavy chain comprising an H-CDR1, H-CDR2 and H-CDR3 of a monoclonal antibody produced by a HIC04-F9 hybridoma having ATCC accession number PTA-7557; and a light chain comprising an L-CDR-1, L-CDR2 and L-CDR3 of a monoclonal antibody produced by the HIC04-F9 hybridoma having ATCC accession number PTA-7557, wherein the monoclonal antibody specifically binds pancreatic endocrine cells.

2. The isolated monoclonal antibody of claim 1, wherein the monoclonal antibody is produced by the HIC04-F9 hybridoma having ATCC accession number PTA-7557.

3. The isolated monoclonal antibody of claim 1, said antibody comprising a human framework region.

4. An isolated antigen-binding fragment of the isolated monoclonal antibody of claim 1, wherein the antigen binding fragment specifically binds pancreatic endocrine cells.

5. The isolated antigen-binding fragment of the monoclonal antibody of claim 4, wherein the antigen-binding fragment is a scFV, a Fv, a Fab, a F(ab')2 or a scFV2 fragment.

6. The isolated monoclonal antibody of claim 1, or an antigen-binding fragment thereof, conjugated to an effector molecule.

7. The isolated monoclonal antibody or antigen-binding fragment of claim 6, wherein the effector molecule is a detectable marker or a toxin.

8. The isolated monoclonal antibody or antigen-binding fragment of claim 7, wherein the detectable marker is a fluorescent marker or a radiolabel.

9. The isolated antibody or antigen-binding fragment of claim 7, wherein the toxin comprises ricin A, abrin, diphtheria toxin or a subunit thereof, *Pseudomonas* exotoxin or a portion thereof, saporin, restrictocin or gelonin.

10. An isolated nucleic acid encoding the monoclonal antibody of claim 1, or encoding an antigen binding fragment of the monoclonal antibody.

11. The isolated nucleic acid of claim 10, operably linked to a promoter.

12. An expression vector comprising the nucleic acid of claim 10.

13. An isolated host cell transformed with the expression vector of claim 12.

14. A hybridoma producing the monoclonal antibody of claim 1.

15. A composition comprising the monoclonal antibody of claim 1 or an antigen-binding fragment thereof and physiologically acceptable carrier.

16. A method for detecting a pancreatic endocrine cell, said method comprising: contacting a cell of interest with the monoclonal antibody of claim 1 or an antigen binding fragment thereof; and detecting binding of the monoclonal antibody or the antigen binding fragment thereof to the cell, wherein binding of the monoclonal antibody or the antigen binding fragment thereof to the cell indicates that the cell is a pancreatic endocrine cell.

17. The method of claim 16, wherein the pancreatic endocrine cell is in vitro.

18. The method of claim 16, wherein the pancreatic endocrine cell is in vivo.

19. The method of claim 17, wherein the pancreatic endocrine cell is isolated from a subject that has a pancreatic endocrine cell tumor or diabetes.

20. A method of isolating a pancreatic endocrine cell, said method comprising: contacting a suspension of pancreatic cells with the monoclonal antibody of claim 1 or an antigen binding fragment thereof to form an immune complex; and isolating the immune complex, thereby isolating the pancreatic endocrine cell.

21. The method of claim 20, further comprising contacting the immune complex with a second antibody that specifically binds the monoclonal antibody of claim 1 or the antigen-binding fragment thereof.

22. The method of claim 20, wherein the monoclonal antibody of claim 1 or the antigen-binding fragment thereof is coupled to a detectable marker.

23. The method of claim 21, wherein the second antibody is coupled to a detectable marker.

24. The method of claim 22, wherein the detectable marker is a fluorescent marker.

25. A method for isolating a pancreatic endocrine cell, said method comprising: contacting cells with the antibody of claim 1; detecting binding of the antibody to the cells; and isolating a cell bound to the antibody, thereby isolating the pancreatic endocrine cell, wherein the pancreatic endocrine cell produces insulin or glucagon.

26. The method of claim 16, wherein the cell is isolated from a human cadaveric islet.

27. The method of claim 16, wherein the cell is differentiated from an embryonic stem cell, an adult stem cell or a progenitor cell.

28. The method of claim 20, wherein the cells are isolated from a human cadaveric islet.

29. The method of claim 20, wherein the cells are differentiated from an embryonic stem cells, an adult stem cell or a progenitor cell.

30. A method for determining the purity of a human cadaveric islet preparation comprising: contacting a human cadaveric islet preparation with the monoclonal antibody of claim 1 or an antigen-binding fragment thereof; and detecting binding of the monoclonal antibody or the antigen-binding fragment thereof to cells therein, wherein the extent of binding of the monoclonal antibody or the antigen binding fragment thereof to the cells of the cadaveric islet preparation indicates the purity of the islet preparation.

31. The method of claim 30, further comprising assessing insulin secretion of the islet preparation.

32. The method of claim 30, wherein the method assesses the suitability of the islet cell preparation for transplantation.

\* \* \* \* \*